United States Patent [19]

Kurome et al.

[11] Patent Number: 5,698,670
[45] Date of Patent: Dec. 16, 1997

[54] AUREOBASIDINS

[75] Inventors: Toru Kurome, Muko; Tetsuya Inoue; Kazutoh Takesako, both of Otsu; Kaoru Inami, Ikeda; Ikunoshin Kato, Uji, all of Japan

[73] Assignee: Takara Shuzo Co., Ltd., Kyoto, Japan

[21] Appl. No.: 505,255
[22] PCT Filed: Dec. 26, 1994
[86] PCT No.: PCT/JP94/02201
§ 371 Date: Aug. 16, 1995
§ 102(e) Date: Aug. 16, 1995
[87] PCT Pub. No.: WO95/18147
PCT Pub. Date: Jul. 6, 1995

[30] Foreign Application Priority Data

Dec. 27, 1993 [JP] Japan ............... HEI-5-346873

[51] Int. Cl.$^6$ ............... C07K 11/02; C07K 5/00; A61K 38/12; A61K 38/00
[52] U.S. Cl. ............... 530/317; 530/323; 514/9; 514/11
[58] Field of Search ............... 530/317, 323; 514/9, 11

[56] References Cited

FOREIGN PATENT DOCUMENTS

| 0 352 092 | 1/1990 | European Pat. Off. . |
|---|---|---|
| 0 443 719 A1 | 8/1991 | European Pat. Off. . |
| 0 500 264 A1 | 8/1992 | European Pat. Off. . |
| 0 507 484 | 10/1992 | European Pat. Off. . |
| 0 352 092 B1 | 10/1993 | European Pat. Off. . |
| 0 581 429 A2 | 2/1994 | European Pat. Off. . |
| 2-138296 | 5/1990 | Japan . |
| 3-22995 | 1/1991 | Japan . |
| 3-44398 | 2/1991 | Japan . |
| 3-220199 | 9/1991 | Japan . |
| 5-39204 | 2/1993 | Japan . |
| 5-279384 | 10/1993 | Japan . |
| 6-65291 | 3/1994 | Japan . |

OTHER PUBLICATIONS

Ikai, et al., NMR Studies of Aureobasidins A and E, Journal of Antibiotics, vol. 44, No. 11, pp. 1199–1207, Nov. 1991.
Ikai, et al., Structures of Aureobasidins B to R, Journal of Antibiotics, vol. 44, No. 11, pp. 1187–1198, Nov. 1991.
Yoshikawa et al., Isolation, Structures, and Antifungal Activities of New Aureobasidins, The Journal of Antibiotics, vol. 46, No. 9, 1993, pp. 1347–1354.

*Primary Examiner*—Cecilia J. Tsang
*Assistant Examiner*—Jennifer Harle
*Attorney, Agent, or Firm*—Pollock, Vande Sande & Priddy

[57] ABSTRACT

This invention relates to Aureobasidins useful as an antifungal agent having broader spectrum. The compound according to this invention includes a cyclic depsipeptide consisting of one hydroxy acid residue having $A^1$, 3 amino acid residues having $C^1$, $F^1$ and $H^1$, respectively, 4 N-methylamino acid residues having $B^1$, $D^1$, $G^1$ and $I^1$, respectively, and 1 cyclic amino acid residue having $E^1$. The typical compound includes one wherein $A^1$ is $CH_3CH_2CH(CH_3)$—, $B^1$ is $(CH_3)_2CH$—, $C^1$ is benzyl, cyclohexylmethyl, p-fluorobenzyl, benzyloxymethyl, benzyloxybenzyl, methoxybenzyl, cyclohexylmethyloxybenzyl or the like, $D^1$ is methyl, benzyl, hydroxymethyl or the like, $E^1$ is —$(CH_2)_3$—, $F^1$ is $CH_3CH_2CH(CH_3)$—, $G^1$ is $(CH_3)_2CH$—, $H^1$ is $(CH_3)_2CHCH_2$— and $I^1$ is $(CH_3)_2C(OH)$—. The compound according to this invention has an excellent activity against not only Candida but also Cryptococcus and Aspergillus.

3 Claims, No Drawings

AUREOBASIDINS

TECHNICAL FIELD

This invention relates to Aureobasidins which are of value as the therapy of fungal infections.

PRIOR ART

Fungi infect internal organs and brain to induce systemic mycosis or the skin, oral cavity and other tissues to induce superficial mycosis in man. They also cause similar infections in pet, domestic and other animals. It is also known that fungi cause a variety of diseases in plants such as orchard trees and vegetables.

The principal causative agents of systemic mycosis in man are fungi of the genus Candida, those of the genus Cryptococcus, and those of the genus Aspergillus. Superficial mycosis in man are caused by fungi of the genus Candida (infecting the skin, oral cavity, vagina, etc.) or those of the genus Trichophyton (infecting the skin of the hand and foot). In addition, a broad spectrum of other fungi are members of the earth's ecology and are regarded as etiologic factors in many infections and pollutions in animals and plants. Against such fungal infections, a variety of countermeasures have been undertaken.

A large number of antifungal agents are known that can be used for the treatment and prevention of fungal infections and pollutions but few are satisfactory enough in safety and efficacy. Among the therapeutic drugs heretofore available for systemic infections in man and animals are Amphotericin B, Flucytosine, Miconazole and Fluconazole but these drugs are not impeccable, either, in efficacy, toxicity and/or potential of expression of resistance. Particularly, only a very few drugs are available that can success fully control systemic infections which are steadily increasing in these years.

Aureobasidins have been disclosed in, inter alia, Japanese Kokai Publication Hei-2-138296, Japanese Kokai Publication Hei-3-22995, Japanese Kokai Publication Hei-3-44398, Japanese Kokai Publication Hei-3-220199, Japanese Kokai Publication Hei-5-279384 and Japanese Kokai Publication Hei-6-65291. Among the Aureobasidins described in the above literature are Aureobasidin A of the following structural formula (4) and its various analogs.

Aureobasidin A is one of the most active and least toxic of all the known Aureobasidins and is active against many pathogenic fungi inclusive of Candida species. However, this substance is not sufficiently active against Aspergillus and not as active against Cryptococcus as against Candida, so that no sufficient therapeutic efficacy can be expected in infections associated with the former fungi.

Many other Aureobasidins are also highly active against Candida but only weakly active against Cryptococcus and little active against Aspergillus.

DESCRIPTION OF THE INVENTION

This invention has for its object to provide a novel class of Aureobasidins which are broader in antifungal spectrum than the hitherto-known Aureobasidins.

In summary, this invention relates to an Aureobasidin compound of general formula (1):

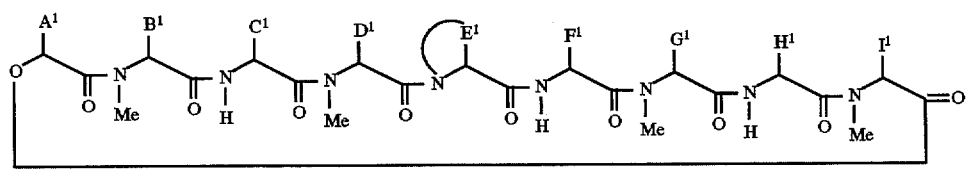

wherein $A^1$, $B^1$, $F^1$, $G^1$ and $H^1$ are the same or different and each represents a straight-chain or branched lower alkyl having 1 to 6 carbon atoms; $C^1$ represents a straight-chain or branched lower alkyl having 1 to 6 carbon atoms, a cycloalkyl having 3 to 7 carbon atoms, benzyloxymethyl, benzyl, a substituted benzyl, phenyl or a substituted phenyl (said substituted benzyl or substituted phenyl means benzyl or phenyl substituted by at least one substituent selected from the class consisting of a straight-chain or branched lower alkoxy having 1 to 6 carbon atoms, cycloalkoxy having 3 to 7 carbon atoms, benzyloxy and halogen); $D^1$ represents a straight-chain or branched lower alkyl having 1 to 6 carbon atoms, hydroxymethyl or benzyl (where $C^1$ is benzyl, $D^1$ is a group other than benzyl and hydroxymethyl); $E^1$ represents a straight-chain alkylene having 1 to 5 carbon atoms; $I^1$ represents a hydroxy-substituted lower alkyl having 1 to 6 carbon atoms.

For the purpose of creating novel Aureobasidin compounds with improved activity against Cryptococcus and Aspergillus, the inventors of this invention synthesized various analogs by chemical synthesis and found that compounds of general formula (1) have higher activity than the known Aureobasidins against Cryptococcus and Aspergillus. This invention has been accomplished as a result.

The compound of the general formula (1) is a cyclic depsipeptide consisting of one hydroxy acid residue having $A^1$, 3 amino acid residues having $C^1$, $F^1$ and $H^1$, respectively, 4 N-methylamino acid residues having $B^1$, $D^1$, $G^1$ and $I^1$, respectively, and 1 cyclic amino acid residue having $E^1$. The above-mentioned $I^1$ has a hydroxy group.

Said $A^1$ is a straight-chain or branched lower alkyl having 1 to 6 carbon atoms, preferably is $(CH_3)_2CH-$ or Formula (4):

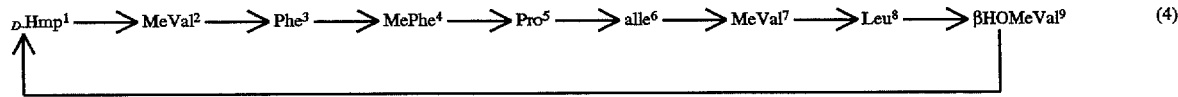

In the above formula, $_D$-Hmp represents 2(R)-hydroxy-3(R)-methylpentanoic acid. All the amino acids are L-types.

$CH_3CH_2CH(CH_3)-$, and the hydroxy acids containing them are 2-hydroxy-3-methylbutanoic acid and 2-hydroxy-3-methylpentanoic acid, respectively.

Said $B^1$ is a straight-chain or branched lower alkyl having 1 to 6 carbon atoms, preferably is $(CH_3)_2CH-$, and the N-methyl amino acid containing it is N-methylvaline.

Said $C^1$ is a straight-chain or branched lower alkyl having 1 to 6 carbon atoms, cycloalkyl having 3 to 7 carbon atoms, benzyl, substituted benzyl, phenyl or substituted phenyl. The lower alkyl of said $C^1$ includes, for example, $CH_3$—, $(CH_3)_2CH$—, $(CH_3)_2CHCH_2$—, $CH_3CH_2CH(CH_3)$— and the like. The amino acids having them are alanine, valine, leucine and isoleucine, respectively, and leucine is preferred. Said cycloalkyl includes, for example, cyclohexyl, cyclohexylmethyl and the like. The amino acid having them are cyclohexylglycine and cyclohexylalanine, respectively, and cyclohexylalanine is preferred. The amino acid having benzyl or phenyl of said $C^1$ is phenylalanine and phenylglycine, respectively. Said benzyl or phenyl may have a substituent of straight-chain or branched lower alkoxy having 1 to 6 carbon atoms, cycloalkoxy having 3 to 7 carbon atoms, benzyloxy or halogen. Said lower alkoxy includes, for example, methyloxy, ethyloxy and the like, and methyloxy is preferred. Said cycloalkoxy includes, for example, cyclohexyloxy, cyclohexylmethyloxy and the like, and cyclohexylmethyloxy is preferred. Said halogen includes, for example, chloro, fluoro and the like, and fluoro is preferred. The amino acid having fluoro includes, for example, p-fluorophenylalanine and the like.

Said $D^1$ is straight-chain or branched lower alkyl having 1 to 6 carbon atoms, hydroxymethyl or benzyl. Said lower alkyl includes, for example, $CH_3$—, $(CH_3)_2CH$—, $(CH_3)_2CHCH_2$—, $CH_3CH_2CH(CH_3)$— and the like. The N-methylamino acid containing them are N-methylalanine, N-methylvaline, N-methylleucine and N-methylisoloeucine respectively, and N-methylalanine and N-methylvaline are preferred. The N-methylamino acid containing said hydroxymethyl and said benzyl respectively is N-methylserine and N-methylphenylalanine. Aureobasidin according to this invention does not include the compound wherein $C^1$ is benzyl, $D^1$ is benzyl or hydroxymethyl.

Said $E^1$ is a straight-chain alkylene having 1 to 5 carbon atoms and preferably, —$(CH_2)_3$—, and the cyclic amino acid having this is proline.

Said $F^1$ is a straight-chain or branched lower alkyl having 1 to 6 carbon atoms, preferably $(CH_3)_2CH$—, $(CH_3)_2CHCH_2$— or $CH_3CH_2CH(CH_3)$—, and amino acid having them are respectively, valine, leucine, isoleucine and alloisoleucine. Alloisoleucine is preferred.

Said $G^1$ is a straight-chain or branched lower alkyl having 1 to 6 carbon atoms, preferably $(CH_3)_2CH$—, and amino acid having it is N-methylvaline.

Said $H^1$ is a straight-chain or branched lower alkyl having 1 to 6 carbon atoms, preferably $(CH_3)_2CH$—, $(CH_3)_2CHCH_2$— or $CH_3CH_2CH(CH_3)$—, and amino acid having them are respectively, valine, leucine, isoleucine and alloisoleucine. Leucine is preferred.

Said $I^1$ is a lower alkyl having 1 to 6 carbon atoms substituted by hydroxy, preferably $(CH_3)_2C(OH)$—. The N-methylamino acid having this is β-hydroxy-N-methylvaline. A typical example of Aureobasidins of general formula (1) includes compounds 1 to 12 shown in Table 1. In Table 1, "•" shows the same amino acid or hydroxy acid as that of compound 1.

TABLE 1

| Compound Number | $A^1$ | $B^1$ | $C^1$ | $D^1$ | $E^1$ |
|---|---|---|---|---|---|
| 1 | (R) CH₃CH₂CH— \| CH₃ | $(CH_3)_2CH$— | $C_6H_5$—$CH_2$— | $CH_3$— | —$(CH_2)_3$— |
| 2 | • | • | $C_6H_5$—$CH_2$— | $(CH_3)_2CH$— | • |
| 3 | • | • | c-$C_6H_{11}$—$CH_2$— | $CH_3$— | • |
| 4 | • | • | pF—$C_6H_4$—$CH_2$— | $CH_3$— | • |
| 5 | • | • | $(CH_3)_2CHCH_2$— | $CH_3$— | • |
| 6 | • | • | c-$C_6H_{11}$—$CH_2$— | $C_6H_5$—$CH_2$— | • |
| 7 | • | • | $C_6H_5$—$CH_2$—O—$CH_2$— | $CH_3$— | • |
| 8 | • | • | c-$C_6H_{11}$—$CH_2$— | $(CH_3)_2CH$— | • |
| 9 | • | • | c-$C_6H_{11}$—$CH_2$— | HO—$CH_2$— | • |
| 10 | • | • | $C_6H_5$—$CH_2$—O—$C_6H_4$—$CH_2$— | $CH_3$— | • |
| 11 | • | • | $CH_3$—O—$C_6H_4$—$CH_2$ab,4 | $CH_3$— | • |
| 12 | • | • | c-$C_6H_{11}$—$CH_2$—O—$C_6H_4$—$CH_2$— | $CH_3$— | • |

| Compound Number | $F^1$ | $G^1$ | $H^1$ | $I^1$ |
|---|---|---|---|---|
| 1 | (R) CH₃CH₂CH— \| CH₃ | $(CH_3)_2CH$— | $(CH_3)_2CHCH_2$— | $(CH_3)_2C(OH)$— |
| 2 | • | • | • | • |
| 3 | • | • | • | • |
| 4 | • | • | • | • |
| 5 | • | • | • | • |
| 6 | • | • | • | • |
| 7 | • | • | • | • |
| 8 | • | • | • | • |
| 9 | • | • | • | • |
| 10 | • | • | • | • |
| 11 | • | • | • | • |
| 12 | • | • | • | • |

In said compounds 1 to 12, all amino acids having $D^1$ are D-types except compound 6, and hydroxy acids having $A^1$ are D-types. In said compounds 1 to 12, all amino acids except hydroxy acids having $A^1$ and amino acids having $D^1$ are L-types. In Table 1, $C_6H_5$—$CH_2$— means benzyl, pF—$C_6H_4$—$CH_2$— means p-fluorobenzyl, $C_6H_5$—$CH_2$—O—$C_6H_4$—$CH_2$— means benzyloxybenzyl, $CH_3$—O—$C_6H_4$—$CH_2$— means methoxybenzyl, $C_6H_5$—$CH_2$—O—$CH_2$— means benzyloxymethyl, $_c$—$C_6H_{11}$—$CH_2$— means cyclohexylmethyl and $_c$—$C_6H_{11}$—$CH_2$—O—$C_6H_4$—$CH_2$— means cyclohexylmethyloxybenzyl, respectively.

The amino acids in the context of this specification including said general formula (1) are abbreviated as follows.

$_D$-Hmp is 2(R)-hydroxy-3(R)-methylpentanoic acid, βHOMeVal is β-hydroxy-N-methylvaline, Cha is cyclohexylalanine, pFPhe is p-fluorophenylalanine, Ser (Bzl) is O-benzylserine, Tyr(Me) is O-methyltyrosine, Tyr (Bzl) is O-benzyltyrosine, and Tyr(c-$C_6H_{11}$—$CH_2$—) is O-cyclohexylmethyltyrosine.

The compound of this invention can be produced by the method of total synthesis described in Japanese Kokai Publication Hei-6-65291. Alternatively, the compound of the invention can also be produced by any semi-synthetic process using peptide fragments prepared from natural Aureobasidin by various chemical and/or enzymatic techniques. When the above-mentioned method of total synthesis or semi-synthesis is employed, the route of cyclizing a linear peptide of the following general formula (5) can be selected with advantage.

For the preparation of the linear peptide described above, it is advantageous to synthesize 2 or 3 peptide fragments and link them together by condensation.

Formula (5):

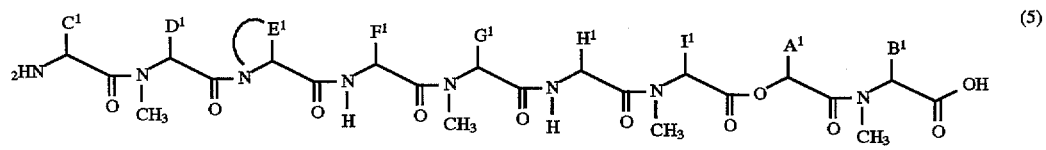

(5)

The above-mentioned method of total synthesis for the compound of general formula (1) wherein $A^1$ stands for $CH_3CH_2CH(CH_3)$—, $B^1$ for $(CH_3)_2CH$—, $C^1$ for benzyl, $D^1$ for $CH_3$—, $E^1$ for —$(CH_2)_3$—, $F^1$ for $CH_3CH_2CH(CH_3)$—, $G^1$ for $(CH_3)_2CH$—, $H^1$ for $(CH_3)_2CHCH_2$—, $I^1$ for $(CH_3)C(OH)$—; the hydroxy acid having $A^1$ is D-type, the amino acid having $D^1$ is D-type, and all the other amino acids are L-types, now described taking Compound 1 of the following general formula (6) as an example.

Formula (6) (Compound 1):

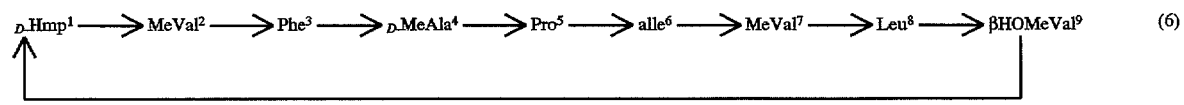

(6)

The above-mentioned method of semi-synthesis is now described taking as an example Compound 9 of the following general formula (7) wherein $C^1$ represents cyclohexylmethyl, $D_1$ represents $HOCH_2$—, and the other residues are identical to those of Compound 1.

Formula (7) (Compound 9):

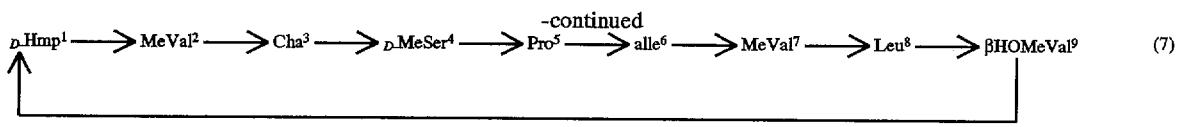

(7)

For the production of Compound 1 by total synthesis, the method comprises synthesizing the three fragment peptides of aIle$^6$→MeVal$^7$ (fragment 1), Leu$^8$→βHOMeVal$^9$→$_D$-

Hmp$^1$ (fragment 2), and MeVal$^2$→Phe$^3$→$_D$-MeAla$^4$→Pro$^5$ (fragment 3), respectively, then condensing fragment 2 and fragment 3 between $_D$-Hmp$^1$ and MeVal$^8$, and finally condensing the resulting fragment 2-fragment 3 peptide and fragment 1 between MeVal$^7$ and Leu$^8$ to provide a linear peptide of the following formula (8). Then, a cyclization is conducted to provide the objective Compound 1 of the formula (6).

Formula (8):

The method of semi-synthesis for the production of Compound 9 typically comprises treating aureobasidin A of formula (4) with anhydrous hydrogen fluoride (HF) and, then, treating it with a prolyl endo-peptidase to prepare aIle$^6$→MeVal$^7$→Leu$^8$→βHOMeVal$^9$→$_D$-Hmp$^1$→MeVal$^2$ (fragment 4).

In the above production process, the prolyl endopeptidase cleaves the peptide bond between Pro$^5$ and aIle$^6$ of the linear nonapeptide (H-Phe→MePhe→Pro→aIle→MeVal→Leu→βHOMeVal→$_D$-Hmp→MeVal-OH) prepared by the above treatment of Aureobasidin A with an acid, e.g. anhydrous hydrogen fluoride, to thereby provide fragment 4. Regarding the conditions of HF treatment, the reaction temperature that can be used is −10° to 50° C., preferably 10° to 30° C., and the reaction time is 10 minutes to 40 hours, preferably 30 minutes to 20 hours. The yield can be increased by controlling the reactant concentration or adding a scavenger such as anisole.

The method of producing fragment 4 from said linear nonapeptide (H-Phe→MePhe→Pro→aIle→MeVal→Leu→βHOMeVal→β$_D$-Hmp→MeVal-OH) is not limited to the above procedure employing a prolyl endo-peptidase but may be a process involving sequential elimination of amino acids from the N-terminus using an amino peptidase or by Edman degradation. However, the procedure employing a prolyl endo-peptidase is most advantageous. The prolyl endo-peptidase mentioned above can be prepared from the bovine brain or microorganisms such as Flavobacterium spp.

In the production of fragment 4, a derivative of the terminal amino acid, such as the benzyloxycarbonyl derivative, of said linear nonapeptide (H-Phe→MePhe→Pro→aIle→MeVal→Leu→βHOMeVal→$_D$-Hmp→MeVal-OH) can also be used as the substrate.

The thus-prepared fragment 4 and synthetic Cha$^3$→$_D$-MeSer$^4$→Pro$^5$ (fragment 5) are condensed between MeVal$^2$ and Cha$^3$ to prepare a linear depsipeptide of the following formula (9).

Formula (9):

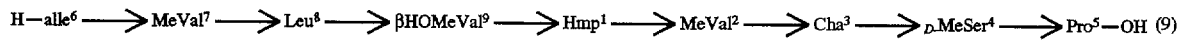

Then, the cyclization is carried out to provide the objective Compound 9 of formula (7).

Selection of the reactants and reagents for use and the conditions of reactions in the respective stages of the above method of total synthesis or semi-synthesis is very important for providing the objective peptide in good yield and high stereochemical purity. Formation of peptide bonds in various stages of the above total synthesis or semi-synthesis can be achieved by various processes such as (1) the process comprising activating the carboxyl group with a water-soluble carbodiimide and HOBt, (2) the process comprising activating the carboxyl group with diphenyl phosphorylazide (DPPA) in the form of a carbonylazide, (3) the process employing (benzotriazolyloxy)tris(dimethylamino) phosphonium hexafluorophosphate (BOP), and most desirably (4) the process employing bromotrispyrrolidinophosphonium hexafluorophosphate (PyBroP) and a base such as diisopropylethylamine (DIEA).

For the formation of a peptide bond, the processes (1) to (3) are generally used but when a peptide bond is formed using an N-methylamino acid as the amine component by such methods, the problems of low yield and racemization are often encountered. However, the above process (4) provides the objective peptide in high yield, avoiding the above problems.

The ester bond between βHOMeVal$^9$ and $_D$-Hmp$^1$ in said total synthesis can be formed by, for example, (5) the process employing PyBroP, (6) the process employing 2,4,6-trichlorobenzoyl chloride and involving a mixed anhydride with βHOMeVal, or preferably (7) the process employing dicyclohexylcarbodiimide (DCC) in combination with a catalyst such as dimethylaminopyridine (DMAP) or 4-pyrrolidinopyridine. By the last-mentioned process, the objective compound can be obtained in good yield. In practicing these processes, the hydroxyl group of βHOMeVal$^9$ may be free or previously protected.

The condensation of fragment 2 and fragment 3 by peptide bond formation between $_D$-Hmp$^1$ and MeVal$^2$ for the synthesis of Compound 1 can be carried out by any of the above processes (1) to (4) but is preferably carried out by process (4) employing PyBroP and a base. By this process, a fragment 2-fragment 3 peptide of high stereochemical purity can be obtained quickly and in good yield.

In the synthesis of Compound 1, where the fragment 2-fragment 3 peptide (Leu$^8$→βHOMeVal$^9$→$_D$-

Hmp$^1$→MeVal$^2$→Phe$^3$→$_D$-MeAla$^4$→Pro$^5$) and fragment 1 (aIle$^8$→MeVal$^7$) are condensed between Leu$^8$ and MeVal$^7$ or in the synthesis of Compound 9 where fragment 4 and fragment 5 are condensed by peptide bond formation between MeVal$^2$ and Phe$^3$, the process employing PyBroP in combination with a base such as DIEA, for instance, can be utilized. However, the preferred process comprises activating the C-terminal carboxyl group with N-ethyl-N'-dimethylaminopropylcarbodiimide (EDC) and 3-hydroxy-4-oxo-3,4-dihydro-1,2,3-benzotriazine (HOOBt). In order that the objective compound of high stereochemical purity may be produced, control of the reaction temperature is important. Generally, the reaction is conducted at −20° to 30° C.

The cyclization in the final stage is carried out by the method which comprises using a linear peptide of the above formula (8) or (9) such that the C-terminal and N-terminal protective groups of the fragment 1-fragment 2-fragment 3 peptide or fragment 4-fragment 5 peptide obtained in the preceding step have been removed beforehand, transforming said linear peptide to a peptide having an activated C-terminal carboxyl group and a free N-terminal amino acid, and reacting the transformed peptide in the presence of a base. The reaction temperature for this cyclization depends on the activated carboxyl group chosen but is generally in the range of −20° to 60° C. and preferably −10° to 30° C. The reaction time for cyclization is several minutes to a few days, preferably a few hours to 24 hours.

In the cyclization procedure described above, activation of the C-terminal carboxyl group can be achieved by conversion to an N-hydroxysuccinimide ester (ONSu) or the activating process using PyBroP. The base that can be used includes but is not limited to DIEA and pyridine.

Referring to the case in which the C-terminal carboxyl group is activated in the form of ONSu, the ONSu ester can be obtained by reacting the linear peptide having a protected N-terminal amino group and a free C-terminal carboxyl group with the hydrochloride of a water-soluble carbodiimide (e.g. EDC) and N-hydroxysuccinimide (HONSu) in an organic solvent such as dimethylformamide (DMF), among other solvents, at −10° to 30° C. The N-terminus of the resulting linear peptide having the C-terminal ONSu active group can be converted to a free amino group or a salt thereof by a deprotection procedure suited to the N-terminal protecting group. As the cyclization proceeds in the presence of a base, the peptide of formula (8) or (9) wherein the C-terminus is a carboxyl group activated in the form of ONSu results ultimately.

When the C-terminal carboxyl group is activated with PyBroP, the compound having an activated C-terminal carboxyl group can be obtained by reacting the peptide of formula (8) or (9) having a free N-terminal amino group or a salt thereof and a free C-terminal carboxyl group with PyBroP in the presence of a base, for example in an organic solvent such as methylene chloride, at a temperature of −10° to 30° C. In this case, the above reaction is accompanied by the cyclization reaction in parallel.

In this cyclization, while the objective Compound 1 of formula (6) or Compound 9 of formula (7) can be obtained by whichever of the above-described two alternative procedures for activating the terminal carboxyl group, the yield of the reaction can be enhanced by meticulous control of reactant concentrations and reaction temperature and judicious selection of the solvent.

In conducting the reaction in each of the above processes, protection of the N-terminal amino group can be carried out with, for example, t-butoxycarbonyl (Boc) and that of the C-terminal carboxyl group with Pac, Bzl and the like. If necessary, these protective groups can be removed by the corresponding deprotection procedures which are known or inferable from the prior art for transformation to the desired compound having a free N-terminal amino group or a salt thereof or a free C-terminal carboxyl group or a salt thereof. A large number of other protective groups are also known for the protection of a free carboxyl group or free amino group and can be utilized as well in the synthesis of the linear peptide of formula (8) or (9) and the synthesis of Compound 1 of formula (6) or Compound 9 of formula (7). Moreover, the hydroxyl group of βHOMeVal$^9$ may be protected, for example with Bzl or methyl, or with trimethylsilyl through a reaction with N,O-bis(trimethylsilyl) trifluoroacetamide (BSTFA). Even when the hydroxyl group of βHOMeVal$^9$ has been thus protected, the above cyclization reaction proceeds just as in the case of the unprotected hydroxy-compound to give the O-protected form of Compound 1 of formula (6) or Compound 9 of formula (7). After completion of the cyclization, the protective group can be removed by the corresponding deprotection procedure to provide Compound 1 of formula (6) or Compound 9 of formula (7).

While the foregoing is a description of the synthetic technology for providing Compound 1 of formula (6) or Compound 9 of formula (7), the cyclic peptide of formula (1) according to this invention can be produced by the same procedures as those described for the synthesis of Compound 1 and Compound 9. Thus, the condensation by way of peptide bond formation can be carried out by any of the above described processes (1) through (4) and preferably by (4) the process employing PyBroP and a base, which provides the stereochemically pure objective compound quickly and in good yield.

The condensation by way of an ester bond between the hydroxy acid residue having A$^1$ and the amino acid residue having I$^1$ can be carried out by any of the processes (5) to (7) described hereinbefore and preferably by (7) the process employing DCC in combination with a catalyst such as DMAP or 4-pyrrolidinopyridine, which provides the objective compound in good yield. The cyclization in the final stage can be carried out by converting the obtained linear depsipeptide to a peptide having an activated C-terminal carboxyl group and a free N-terminal amino group and reacting the converted peptide in the presence of a base. In this procedure, activation of the C-terminus can be carried out by the active ester involving the formation of ONSu or the activating process using PyBroP and, as the base mentioned above, DIEA, pyridine or the like can be employed.

The protection of N-terminal, C-terminal and hydroxyl group in each steps of this reaction and their removal may be conducted as the same manner as the synthesis of compound 1 of formula (6) and compound 9 of formula (7).

Thus the novel Aureobasidins whose minimum growth inhibitory concentration (MIC, µg/ml) against Cryptococcus and Aspergillus is very low and having no toxicological effect can be produced.

For administration of the compound of this invention as a drug to man or other animals, it can be administered as it is or as formulated beforehand into a pharmaceutical composition containing 0.01 to 99.5%, preferably 0.5 to 90%, of the compound in a pharmaceutically acceptable, nontoxic and inert excipient.

Said excipient may be, for example, one or more solid, semisolid or liquid diluents, fillers and/or other formulation auxiliaries. Such a pharmaceutical composition is preferably administered in unit dosage forms.

Said pharmaceutical composition can be administered intravenously, orally, into tissues, topically (e.g. though the skin, etc.) or rectally. Of course, dosage forms suitable for the respective routes of administration should be employed.

The dosage as an antifungal agent should preferably be selected according to the patient's age, body weight and other characteristics, the route of administration and the nature and severity of the disease. The generally recommended dosage to an adult human is 10 to 2000 mg/body/day. The required dosage may be somewhat less or more, depending on individual cases. The pharmaceutical composition may also be administered in 2 or 3 divided doses.

For oral administration, either solid or liquid unit dosage forms, such as neat powders, powders, tablets, dragees, capsules, drops, sublingual, etc. can be provided.

For non-oral administration, liquid unit dosage forms for subcutaneous, intramuscular or intravenous administration, such as solutions and suspensions, can be utilized. Thus, these preparations can be manufactured by suspending or dissolving a predetermined amount of the active compound in an injectable nontoxic liquid vehicle, such as an aqueous or oily medium, and sterilizing the resulting suspension or solution.

For the local administration (e.g. through the skin, etc.), liquid, cream, powder, past, gel, ointment or other external application form can be utilized. Thus, these preparations can be manufactured by mixing the dose amount of the compound of this invention with one or more of flavor, colorant, filler, detergent, moisturelizer, skin softener, geller, vehicle, preservatives, stabilizer and the like acceptable for external application.

For rectal administration, the compound of this invention can be used as a suppository formed mixing with the solid having a low melting point such as higher esters such as parmitic miristyl ester, polyethyleneglycol, cacao oil and mixture thereof.

BEST MODE FOR IMPLEMENT THE INVENTION

The following examples are intended to describe this invention in further detail and should by no means be interpreted as defining the scope of the invention.

EXAMPLE 1

Synthesis of cyclo($_L$-aIle-$_L$-MeVal-$_L$-Leu-$_L$-βHOMeVal-$_D$-Hmp-$_L$-MeVal-$_L$-Phe-$_D$-MeAla-$_L$-Pro) (Compound 1)

a) Boc-$_D$-MeAla-OH

To 48 ml of a solution of Boc-$_D$-Ala-OH (3.0 g, 15.9 mmol) in tetrahydrofuran (THF) was added 60% sodium hydride (1.9 g, 47.6 mmol) under ice-cooling and the mixture was stirred for 10 minutes. Then, methyl iodide (7.9 ml, 127 mmol) was added and the mixture was further stirred at room temperature for 22 hours. The reaction mixture was then concentrated under reduced pressure, ice-cooled, acidified with 10% citric acid-H$_2$O, and extracted with ethyl acetate. The extract was washed with saturated NaCl-H$_2$O, dried over magnesium sulfate, and concentrated under reduced pressure. The residue was crystallized from hexane and the crystal crop was washed with hexane to provide the title compound. Yield 3.07 g (94.8%).

b) Boc-$_D$-MeAla-$_L$-Pro-OPac

In methylene chloride (12 ml) was dissolved Boc-D-MeAla-OH (1.50 g, 7.38 mmol) as well as HCl.H-$_L$-Pro-OPac (1.53 g, 5.68 mmol) followed by addition PyBroP (3.44 g, 7.38 mmol) and DIEA (3.96 ml, 22.7 mmol) under ice-cooling. The mixture was stirred under ice-cooling for 3 hours. This reaction mixture was concentrated under reduced pressure, diluted with ethyl acetate, and washed serially with 10% citric acid-H$_2$O, saturated sodium chloride-H$_2$O, saturated sodium hydrogen carbonate-H$_2$O, and saturated sodium chloride-H$_2$O. The washed solution was dried over magnesium sulfate and concentrated under reduced pressure. The residue was then purified by medium-pressure silica gel column chromatography (silica gel 200 g, eluted with chloroform and chloroform-methanol 100:1). The eluate was concentrated under reduced pressure and crystallized from hexane and the crystal crop was washed with hexane to provide the title compound. Yield 1.90 g (78.0%).

c) HCl.H-$_D$-MeAla-$_L$-Pro-OPac

To Boc-$_D$-MeAla-$_L$-Pro-OPac (1.7 g, 4.06 mmol) was added 4.0N HCl/dioxane (30 ml) and the mixture was allowed to stand at room temperature for 40 minutes. The reaction mixture was concentrated under reduced pressure, crystallized from ether, and washed with ether to provide the title compound. Yield 1.38 g (95.8%).

d) Boc-$_L$-Phe-D-MeAla-$_L$-Pro-OPac

To a solution of Boc-$_L$-Phe-OH (1.26 g, 4.76 mmol) and HCl.H-$_D$-MeAla-$_L$-Pro-OPac (1.30 g, 3.66 mmol) in methylene chloride (10 ml) was added PyBroP (2.22 g, 4.76 mmol) as well as DIEA (2.55 ml, 14.6 mmol) under ice-cooling and the mixture was stirred under ice-cooling for 2 hours. This reaction mixture was concentrated under reduced pressure and the residue was diluted with ethyl acetate and washed serially with 10% citric acid-H$_2$O, saturated sodium chloride-H$_2$O, saturated sodium hydrogen carbonate-H$_2$O, and saturated sodium chloride-H$_2$O. The washed solution was dried over magnesium sulfate and concentrated under reduced pressure. The residue was then purified by medium-pressure silica gel column chromatography (silica gel 200 g, eluted with toluene-ethyl acetate=3:1 and 1:1) to provide the title compound. Yield 1.76 g (84.9%).

e) HCl.H-$_L$-Phe-$_D$-MeAla-$_L$-Pro-OPac

To Boc-$_L$-Phe-$_D$-MeAla-$_L$-Pro-OPac (1.70 g, 3.01 mmol) was added 4.0N-hydrogen chloride/dioxane (30 ml)and the mixture was allowed to stand at room temperature for 30 minutes. This reaction mixture was concentrated under reduced pressure and the residue was crystallized from ether and washed with ether to provide the title compound. Yield 1.63 g (100%).

f) Boc-$_L$-MeVal-$_L$-Phe-$_D$-MeAla-$_L$-Pro-OPac

To a solution of Boc-$_L$-MeVal-OH (898 mg, 3.88 mmol) in methylene chloride (9 ml) was added HCl.H-$_L$-Phe-$_D$-MeAla-$_L$-Pro-OPac (1.45 g, 2.99 mmol) as well as PyBroP (1.81 g, 3.88 mmol) under ice-cooling. Then, after addition of DIEA (2.08 ml, 12.0 mmol), the mixture was stirred under ice-cooling for 16 hours. This reaction mixture was concentrated under reduced pressure, diluted with ethyl acetate, and washed serially with 10% citric acid-H$_2$O, saturated sodium chloride-H$_2$O, saturated sodium hydrogen carbonate-H$_2$O, and saturated sodium chloride-H$_2$O. The washed solution was dried over magnesium sulfate and concentrated under reduced pressure and the residue was purified by medium-pressure silica gel column chromatography (silica gel 200 g, eluted with toluene-ethyl acetate=2:1 and 1:1) to provide the title compound. Yield 1.67 g (82.3%).

g) HCl. H-$_L$-MeVal-$_L$-Phe-$_D$-MeAla-$_L$-Pro-OPac

To Boc-$_L$-MeVal-$_L$-Phe-$_D$-MeAla-$_L$-Pro-OPac (1.00 g, 1.47 mmol) was added 4.0N-HCl/dioxane (18.4 ml) and the mixture was allowed to stand at room temperature for 50 minutes. This reaction mixture was concentrated under reduced pressure, crystallized from ether, and washed with ether to provide the title compound. Yield 838 mg (92.7%).

h) Boc-$_{DL}$-βHOMeVal-OBzl

To a suspension of H-$_{DL}$-βHOMeVal-OH (38.6 mg, 0.264 mmol) in DMF (0.57 ml) was added BSTFA (0.56 ml, 2.11 mmol) under ice-cooling and the mixture was stirred at room temperature for 1 hour. To this reaction mixture was added di-t-butyl-dicarbonate (72.8 μl, 0.317 mmol) under ice-cooling and the mixture was stirred at room temperature for 1.5 hours. This reaction mixture was concentrated under reduced pressure, diluted with 10% citric acid-H$_2$O, and washed with saturated sodium chloride-H$_2$O. The washed solution was dried over magnesium sulfate and concentrated under reduced pressure. The residual oil was dissolved in ethyl acetate (0.5 ml), followed by addition of triethylamine (55.0 μl, 0.396 mmol) and benzyl bromide (62.8 μl, 0.528 mmol) under ice-cooling. The mixture was stirred under ice-cooling for 5 minutes and, then, at room temperature for 48 hours. The reaction mixture was then concentrated under reduced pressure and purified by preparative silica gel thin layer chromatography (developed with chloroform-methanol=19:1) to provide the title compound. Yield 60.7 mg (68.1%).

i) HCl-$_{DL}$-βHOMeVal-OBzl

To Boc-$_{DL}$-βHOMeVal-OBzl (472 mg, 1.40 mmol) was added 5.5N HCl/dioxane (29.5 ml) and the mixture was allowed to stand at room temperature for 1.5 hours. This reaction mixture was concentrated under reduced pressure, crystallized from ether, and washed with ether to provide the title compound. Yield 367 mg (95.7%).

j) Boc-$_L$-Leu-$_{DL}$-βHOMeVal-OBzl

To a solution of Boc-$_L$-Leu-OH.H$_2$O (1.34 g, 5.39 mmol) in methylene chloride (10 ml) was added HCl.H-$_{DL}$-βHOMeVal-OBzl (981.1 mg, 3.59 mmol) as well as PyBroP (2.52 g, 5.39 mmol) under ice-cooling, followed by addition of DIEA (2.50 ml, 14.4 mmol), and the mixture was stirred under ice-cooling for 1 hour and, then, at room temperature for 8 hours. This reaction mixture was concentrated under reduced pressure and the residue was diluted with ethyl acetate and washed serially with 10% citric acid-H$_2$O, saturated sodium chloride-H$_2$O, saturated sodium hydrogen carbonate-H$_2$O, and saturated sodium chloride-H$_2$O. The washed solution was dried over magnesium sulfate and concentrated under reduced pressure and the residue was purified by medium-pressure silica gel column chromatography (silica gel 40 g, eluted with toluene-ethyl acetate=3:1). The eluate was concentrated under reduced pressure and crystallized from hexane to provide the title compound. Yield 1.05 g (65.2%).

k) Boc-$_L$-Leu-$_{DL}$-βHOMeVal-OH

To a solution of Boc-$_L$-Leu-$_{DL}$-βHOMeVal-OBzl (43.5 mg, 96.5 μmol) in methanol (40 ml) was added palladium black (40 mg) and, then, hydrogen gas was bubbled through the solution at room temperature for 50 minutes. The catalyst was then filtered off and the filtrate was concentrated under reduced pressure to provide the title compound. Yield 30.6 mg (87.9%).

l) Boc-$_L$-Leu-$_L$-βHOMeVal-$_D$-Hmp-OPac

In THF (4.3 ml) was dissolved Boc-$_L$-Leu-$_{DL}$-βHOMeVal-OH (744 mg, 2.15 mmol) as well as phenacyl 2(R)-hydroxy-3(R)-methylpentanoate ($_D$-Hmp-OPac) (589 mg, 2.36 mmol) and 4-pyrrolidinopyridine (95.6 mg, 0.65 mmol), followed by addition of DCC (487 mg, 2.36 mmol) under ice-cooling. The mixture was stirred under ice-cooling for 1 hour, after which it was allowed to warm up to room temperature and stirred for 18 hours.

This reaction mixture was concentrated under reduced pressure and diluted with ethyl acetate, and the insoluble matter was filtered off. The filtrate was washed serially with 10% citric acid-H$_2$O, saturated sodium chloride-H$_2$O, saturated sodium hydrogen carbonate-H$_2$O, and saturated sodium chloride-H$_2$O. The washed solution was dried over magnesium sulfate and concentrated under reduced pressure. The residue was purified by medium-pressure silica gel column chromatography (silica gel 80 g, eluted with toluene-ethyl acetate=5:1) to provide Boc-$_L$-Leu-$_{DL}$-βHOMeVal-$_D$-Hmp-OPac (yield 1.00 g, 78.7%). This compound was further subjected to medium-pressure silica gel column chromatography (silica gel 200 g, eluted with toluene-ethyl acetate=15:1 and 10:1) for fractionation of diastereomers to provide the title compound. Yield 357 mg (56.2%, based on the L-L isomer of Boc-$_L$-Leu-$_{DL}$-βHOMeVal-OH).

m) Boc-$_L$-Leu-$_L$-βHOMeVal-$_L$-Hmp-OH

In 90% acetic acid/water (18.5 ml) was dissolved Boc-$_L$-Leu-$_L$-βHOMeVal-$_D$-Hmp-OPac (220 mg, 0.37 mmol) followed by addition of zinc dust (3.60 g, 55.5 mmol) under ice-cooling and ultrasonic agitation. The mixture was further stirred by sonication under ice-cooling for 7.5 hours. The insoluble matter was then filtered off and the filtrate was concentrated under reduced pressure. The residue was diluted with 10% citric acid-water and extracted with ethyl acetate.

The extract was washed with saturated sodium chloride-H$_2$O, dried over magnesium sulfate, and concentrated under reduced pressure. The residue was purified by medium-pressure silica gel column chromatography (silica gel 10 g, eluted with chloroform-methanol-acetic acid=50:1:0.5) to provide the title compound. Yield 133 mg (73.7%).

n) HCl.H-$_L$-MeVal-OPac

To a solution of Boc-$_L$-MeVal-OH (4.94 g, 21.4 mmol) in acetone (50 ml) was added triethylamine (3.30 ml, 23.8 mmol) as well as phenacyl bromide (4.77 g, 24.0 mmol) under ice-cooling and the mixture was stirred under ice-cooling for 1 hour and further at room temperature for 2 hours. This reaction mixture was concentrated, diluted with ethyl acetate, and washed serially with water, saturated sodium hydrogen carbonate-H$_2$O, and saturated sodium chloride-H$_2$O. The washed solution was dried over magnesium sulfate and concentrated under reduced pressure. To the residue was added 5.5N HCl/dioxane (77.8 ml, 0.428 mmol) and the mixture was allowed to stand at room temperature for 30 minutes. This reaction mixture was concentrated under reduced pressure, crystallized from ether and washed with ether to provide the title compound. Yield 6.08 g (99.3%).

o) Boc-$_L$-aIle-$_L$-MeVal-OPac

In methylene chloride (10 ml) was dissolved HCl.H-$_L$-MeVal-OPac (1.12 g, 4.18 mmol) followed by addition of Boc-$_L$-aIle-OH (1.06 g, 4.59 mmol) as well as PyBroP (2.57 g, 5.49 mmol) and DIEA (2.65 ml, 15.2 mmol) under ice-cooling. The mixture was stirred under ice-cooling for 30 minutes and then at room temperature for 17 hours. This reaction mixture was concentrated under reduced pressure, diluted with ethyl acetate, and washed serially with saturated sodium carbonate-H$_2$O, saturated sodium chloride-H$_2$O, 10% citric acid-H$_2$O, and saturated sodium chloride-H$_2$O. The washed solution was dried over magnesium sulfate and concentrated under reduced pressure and the residue was purified by medium-pressure silica gel column chromatography (silica gel 80 g, eluted with chloroform) to provide the title compound. Yield 764 mg (36.0%).

p) Boc-$_L$-aIle-$_L$-MeVal-OH

In 90% acetic acid/water (70 ml) was dissolved Boc-$_L$-aIle-$_L$-MeVal-OPac (657 mg, 1.42 mmol), followed by addition of zinc dust (4.64 g, 71.0 mmol) under ice-cooling and ultrasonic agitation for 7.5 hours. The insoluble matter was then filtered off and the filtrate was concentrated under reduced pressure. The residue was diluted with ethyl acetate and washed serially with 10% citric acid-$H_2O$ and saturated sodium chloride $H_2O$. The washed solution was dried over magnesium sulfate and concentrated under reduced pressure. The residue was crystallized from hexane and washed with hexane to provide the title compound. Yield 325 mg (66.5%).

q) Boc-$_L$-Leu-$_L$-βHOMeVal-$_D$-Hmp-$_L$-MeVal-$_L$-Phe-$_D$-MeAla-$_L$-Pro-OPac

To a solution of Boc-$_L$-Leu-$_L$-βHOMeVal-$_D$-Hmp-OH (60.0 mg, 0.123 mmol) in methylene chloride (400 μl) was added HCl. H-$_L$-MeVal-$_L$-Phe-$_D$-MeAla-$_L$-Pro-OPac (114 mg, 0.184 mmol) as well as PyBroP (74.6 mg, 0.16 mmol) under ice-cooling, followed by addition of DIEA (86.0 μl, 0.491 mmol). The mixture was stirred under ice-cooling for 2 hours and then at room temperature for 13 hours. This reaction mixture was concentrated under reduced pressure, diluted with ethyl acetate, and washed serially with 10% citric acid-$H_2O$, saturated sodium chloride-$H_2O$, saturated sodium hydrogen carbonate-$H_2O$, and saturated sodium chloride-$H_2O$. The washed solution was dried over magnesium sulfate and concentrated under reduced pressure and the residue was purified by medium-pressure silica gel column chromatography (silica gel 20 g, eluted with toluene-ethyl acetate=2:1 and 3:2) to provide the title compound. Yield 97.4 mg (75.5%).

r) HCl.H-$_L$-H-$_L$-Leu-$_L$-βHOMeVal-$_D$-Hmp-$_L$-MeVal-$_L$-Phe-$_D$-MeAla-$_L$-Pro-OPac

To Boc-$_L$-Leu-$_L$-βHOMeVal-$_D$-Hmp-$_L$-MeVal-$_L$-Phe-$_D$-MeAla-$_L$-Pro-OPac (85 mg, 81.0 μmol) was added trifluoroacetic acid (500 μl, 6.48 mmol) under ice-cooling and the mixture was allowed to stand under ice-cooling for 30 minutes. This reaction mixture was concentrated under reduced pressure and, after addition of ether, 4.0N HCl/dioxane (41 μl, 162 μmol) was added under ice-cooling. The mixture was allowed to stand at room temperature for 30 minutes. The resulting crystals were washed with ether to provide the title compound. Yield 59.2 mg (74.2%).

s) Boc-$_L$-aIle-$_L$-MeVal-$_L$-Leu-$_L$-βHOMeVal-$_D$-Hmp-$_L$-MeVal-$_L$-Phe-$_D$-MeAla-$_L$-Pro-OPac

In DMF(200 μl) was dissolved Boc-$_L$-aIle-$_L$-MeVal-OH (29.0 mg, 83.7 μmol) and HCl.H-$_L$-Leu-$_L$-βHOMeVal-$_D$-Hmp-$_L$-MeVal-$_L$-Phe-$_D$-MeAla-$_L$-Pro-OPac (55.0 mg, 55.8 μmol), and after HOOBt (11.0 mg, 67.0 μmol) was added under ice-cooling, a water-soluble carbodiimide (12.9 μl, 72.5 μmol) was added. The mixture was stirred under ice-cooling for 2 hours. The mixture was further stirred at room temperature for 17 hours, after which it was diluted with ethyl acetate and washed serially with 10% citric acid-$H_2O$, saturated sodium chloride-$H_2O$, saturated sodium hydrogen carbonate-$H_2O$, and saturated sodium chloride-$H_2O$. The washed solution was dried over magnesium sulfate and concentrated under reduced pressure and the residue was purified by preparative silica gel thin layer chromatography (developed with benzene-acetone=3:1 and eluted with ethyl acetate) to provide the title compound. Yield 60.6 mg (85.1%).

t) Boc-$_L$-aIle-$_L$-MeVal-$_L$-Leu-$_L$-βHOMeVal-$_D$-Hmp-$_L$-MeVal-$_L$-Phe-$_D$-MeAla-$_L$-Pro-OH

In 90% acetic acid-water (2.0 ml) was dissolved Boc-$_L$-aIle-$_L$-MeVal-$_L$-Leu-$_L$-βHOMeVal-$_D$-Hmp-$_L$-MeVal-$_L$-Phe-$_D$-MeAla-$_L$-Pro-OPac (50.0 mg, 39.2 μmol) followed by addition of zinc dust (513 mg, 7.84 mmol) under ice-cooling and the mixture was subjected to ultrasonic agitation under ice-cooling for 1 hour. The insoluble matter was filtered off and the filtrate was concentrated under reduced pressure and the residue was diluted with 10% citric acid-water and extracted with ethyl acetate. The extract was washed with saturated sodium chloride-$H_2O$, dried over magnesium sulfate, and concentrated under reduced pressure to provide the title compound. Yield 48.3 mg.

u) HCl.H-$_L$-aIle-$_L$-MeVal-$_L$-Leu-$_L$-βHOMeVal-$_D$-Hmp-$_L$-MeVal-$_L$-Phe-$_D$-MeAla-$_L$-Pro-OH

To Boc-$_L$-aIle-$_L$-MeVal-$_L$-Leu-$_L$-βHOMeVal-$_D$-Hmp-$_L$-MeVal-$_L$-Phe-$_D$-MeAla-$_L$-Pro-OH (48.3 mg, 39.2 μmol) was added trifluoroacetic acid (604 μl, 7.84 mmol) under ice-cooling and the mixture was allowed to stand under ice-cooling for 30 minutes. This reaction mixture was concentrated under reduced pressure and, after addition of ether, 4.0N HCl/dioxane (29.5 μl, 118 μmol) was added under ice-cooling. The mixture was allowed to stand under ice-cooling for 30 minutes. The resulting crystals were washed with ether to provide the title compound. Yield 33.3 mg (78.7%).

v) Cyclo ($_L$-aIle-$_L$-MeVal-$_L$-Leu-$_L$-βHOMeVal-$_D$-Hmp-$_L$-MeVal-$_L$-Phe-$_D$-MeAla-$_L$-Pro) (Compound 1)

In methylene chloride (11 ml) was dissolved HCl.H-$_L$-aIle-$_L$-MeVal-$_L$-Leu-$_L$-βHOMeVal-$_D$-Hmp-$_L$-MeVal-$_L$-Phe-$_D$-MeAla-$_L$-Pro-OH (23.0 mg, 21.3 μmol) as well as DIEA (7.4 μl, 42.6 μmol) and this solution was added dropwise to a solution of PyBroP (49.4 mg, 106 μmol) and DIEA (18.6 μl, 106 μmol) in methylene chloride (11 ml) at room temperature over a period of 4 hours. The mixture was further stirred at room temperature for 20 hours. This reaction mixture was concentrated under reduced pressure and the residue was diluted with ethyl acetate and washed serially with 10% citric acid-$H_2O$, saturated sodium chloride-$H_2O$, saturated sodiumhydrogen carbonate-$H_2O$ and saturated sodium chloride-$H_2O$. The washed solution was dried over magnesium sulfate and concentrated under reduced pressure and the residue was purified by preparative silica gel thin layer chromatography (developed and eluted with chloroform-methanol=19:1) to provide the title compound. Yield 12.1 mg (55.5%).

Physiochemical properties of the title compound are shown below.

$^1$H-NMR (CDCl$_3$, 270 MHz): δ8.62, 7.95, 7.67 (total 3H, NH), 7.35–7.11 (total 5H, aromatic H), 5.79, 5.44–5.22, 4.97, 4.88, 4.73–4.56, 4.30, 4.04, 3.44 (total 10H), 3.33, 3.32, 3.20, 2.85 (total 12H, NCH$_3$), 1.09–0.71 (CH$_3$), and others.

EXAMPLE 2

Synthesis of cyclo($_L$-aIle-$_L$-MeVal-$_L$-Leu-$_L$-βHOMeVal-$_D$-Hmp-$_L$-MeVal-$_L$-Phe-$_D$-MeVal-$_L$-Pro) (Compound 2)

a) H-$_L$-Phe-$_L$-MePhe-$_L$-Pro-$_L$-aIle-$_L$-MeVal-$_L$-Leu-$_L$-βHOMeVal-$_D$-Hmp-$_L$-MeVal-OH (opening the ring of Aureobasidin A by HF)

Anhydrous hydrogen fluoride (200 ml) was added into Aureobasidin A (6.0 g, 5.45 mmol) in cooling bath of dry ice-methanol, and then stirred at room temperature for 1.5 hours. After hydrogen fluoride was distilled off under reduced pressure, residue was lyophilized from dioxane. This was purified by high performance liquid chromatography (column: Soken Pack C-18, 60×500 mm, eluted by 50 to 100% of acetonitrile/0.05% aq. TFA) to provide the title compound. Yield 1.81 g (29.7%).

b) Z-$_L$-Phe-$_L$-MePhe-$_L$-Pro-$_L$-aIle-$_L$-MeVal-$_L$-Leu-$_L$-βHOMeVal-$_D$-Hmp-$_L$-MeVal-OH (wherein Z represents benzyloxycarbonyl)

To dispersion of H-$_L$-Phe-$_L$-MePhe-$_L$-Pro-$_L$-aIle-$_L$-MeVal-$_L$-Leu-$_L$-βHOMeVal-$_D$-Hmp-$_L$-MeVal-OH (200 mg, 0.179 mmol) in DMF (3.6 ml), triethylamine (50.2 µl, 0.358 mmol) and benzyloxycarbonylsuccineimide (53.5 mg, 0.215 mmol) were added and stirred under ice-cooling for 1.5 hours. After concentrated under reduced pressure, precipitate was filtered out by addition of ethyl acetate and washed by 10% citric acid-H₂O and saturated sodium chloride-H₂O. After dried over magnesium sulfate, concentrated under reduced pressure and the residue was purified by medium pressure silica gel column chromatography (eluted by chloroform-methanol-acetic acid 100:2:2) to provide the title compound. Yield 183 mg (81.5%).

c) HCl.H-$_L$-aIle-$_L$-MeVal-$_L$-Leu-$_L$-βHOMeVal-$_D$-Hmp-$_L$-MeVal-OH

Z-$_L$-Phe-$_L$-MePhe-$_L$-Pro-$_L$-aIle-$_L$-MeVal-$_L$-Leu-$_L$-βHOMeVal-$_D$-Hmp-$_L$-MeVal-OH (100 mg, 79.8 mmol) (wherein Z represents benzyloxycarbonyl) in ethanol (10 ml) was added to 50 mM potassium-phosphate buffer (pH 7.0, 89 ml). After stood at 30° C. for 10 minutes, 50 mM potassium-phosphate buffer (pH 7.0, 1.2 ml) in which pro-lylendopeptidase (Seikagakukogyo) (600 unit) was added and stirred for 72 hours, precipitate was removed by centrifugation (at 700 r.p.m. for 10 minutes) and the supernatant was concentrated under reduced pressure. The resulting residue was purified by high performance liquid chromatography (column:YMC C-180DS, eluted by 30 to 90% acetonitrile/0.05% aq. TFA) to provide the title compound. Yield 59.1 mg (100%).

d) Boc-$_L$-aIle-$_L$-MeVal-$_L$-Leu-$_L$-βHOMeVal-$_D$-Hmp-$_L$-MeVal-OH

To HCl.H-$_L$-aIle-$_L$-MeVal-$_L$-Leu-$_L$-βHOMeVal-$_D$-Hmp-$_L$-MeVal-OH (57.7 mg, 81.0 µmol) in dioxan/water (2:1) were added triethylamine (14.6 µl, 105 µmol) and di-t-butyl-dicarbonate (24.0 µl, 105 µmol) and stirred for 3.5 hours at room temperature. After concentrated under reduced pressure, ethyl acetate was added and the mixture was washed by 10% citric acid-H₂O and saturated sodium chloride-H₂O. After dried over magnesium sulfate, the solution was concentrated under reduced pressure and the resulting residue was purified by preparative silica gel thin layer chromatography (developed with chloroform-methanole:acetic acid 100:1:2, extracted with chloroform::methanol 10:1) to provide the title compound. Yield 51.2 mg (77.8%).

e) Boc$_D$-MeVal-OH

The title compound was obtained as the same manner as Example 1 a) using Boc-$_D$-Val-OH (2.0 g, 9.21 mmol), 60% sodium hydride (1.1 g, 27.6 mmol) and methyl iodide (4.56 ml, 73.6 mmol). Yield 1.54 g (72.5% ).

f) Boc-$_D$-MeVal-$_L$-Pro-OPac

The title compound was obtained as the same manner as Example 1 b) using Boc-$_D$-MeVal-OH (300 mg, 1.30 mmol), HCl.H-$_L$-Pro-OPac (291 mg, 1.08 mmol), PyBroP (606 mg, 1.30 mmol) and DIEA (753 µl, 4.32 mmol). Yield 372 mg (77.2%).

g) HCl.H-$_D$-MeVal-$_L$-Pro-OPac

The title compound was obtained as the same manner as Example 1 c) using Boc-$_D$-MeVal-$_L$-Pro-OPac (350 mg, 0.784 mmol) in 4.0N hydrogen chloride/dioxane (5.88 ml). Yield 292 mg (97.3%).

h) Boc-$_L$-Phe-$_D$-VeBal-$_L$-Pro-OPac

The title compound was obtained as the same manner as Example 1 d) using Boc-$_L$-Phe-OH (180 mg, 0.679 mmol), HCl.H-$_D$-MeVal-$_L$-Pro-OPac (200 mg, 0.522 mmol), PyBroP (317 mg, 0.679 mmol) and DIEA (364 µl, 2.09 mmol). Yield 281 mg (90.7%).

i) HCl.H-$_L$-Phe-$_D$-VeBal-$_L$-Pro-OPac

The title compound was obtained as the same manner as Example 1 e) using Boc-$_L$-Phe-$_D$-VeBal-$_L$-Pro-OPac (190 mg, 0.320 mmol) in 4.0N hydrogen chloride/dioxane (4.2 ml). Yield 169 mg (99.4%).

j) Boc-$_L$-aIle-$_L$-MeVal-$_L$-Leu-$_L$-βHOMeVal-$_D$-Hmp-$_L$-MeVal-$_L$-Phe-$_D$-MeVal-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (35.0 mg, 43.1 µmol), HCl.H-$_L$-Phe-$_D$-MeVal-$_L$-Pro-OPac (34.2 mg, 64.6 µmol), HOOBt (8.7 mg, 64.6 µmol) and water soluble carbodiimide (11.4 µl, 64.6 µmol). Yield 34.6 mg (62.3%)

k) Boc-$_L$-aIle-$_L$-MeVal-$_L$-Leu-$_L$-βHOMeVal-$_D$-Hmp-$_L$-MeVal-$_L$-Phe-$_D$-MeVal-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Phe-$_D$-MeVal-$_L$-Pro-Oac (31.0 mg, 24.1 µmol), 90% acetic acid/water (1.2 ml), zinc dust (313 mg, 4.82 mmol). Yield 30.0 mg.

l) HCl.H-$_L$-aIle-$_L$-MeVal-$_L$-Leu-$_L$-βHOMeVal-$_D$-Hmp-$_L$-MeVal-$_L$-Phe-$_D$-MeVal-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Phe-$_D$-MeVal-$_L$-Pro-OH (30.0 mg, 25.7 µmol), trifluoroacetic acid (396 µl, 5.14 mmol) in 4.0N hydrogen chloride/dioxane (12.9 µl, 51.4 µmol). Yield 19.6 mg (73.6%).

m) cyclo($_L$-aIle-$_L$-MeVal-$_L$-Leu-$_L$-βHOMeVal-$_D$-Hmp-$_L$-MeVal-$_L$-Phe-$_D$-MeVal-$_L$-Pro) (Compound 2)

The title compound was obtained as the same manner as Example 1 v) using a solution of HCl.H-$_L$-aIle-$_L$-MeVal-$_L$-Leu-$_L$-βHOMeVal-$_D$-Hmp-$_L$-MeVal-$_L$-Phe-$_D$-MeVal-$_L$-Pro-OH (15.0 mg, 13.6 µmol), DIEA (4.7 µl, 27.2 µmol) in methylene chloride (6.8 ml), and a solution of PyBroP (31.7 mg, 67.9 µmol) and DIEA (11.8 µl, 67.9 µmol) in methylene chloride (6.8 ml). Yield 5.0 mg (35.0%).

The physicochemical properties of the title compound are shown below.

¹H-NMR (CDCl₃, 270 MHz): δ8.78, 8.10, 7.48 (total 3H, NH), 7.35–7.09 (total 5H, aromatic H), 5.78, 5.39, 5.20, 4.98–4.94, 4.80, 4.53, 4.37–4.31, 4.13, 3.45 (total 10H), 3.33, 3.22, 2.78 (total 12H, NCH₃), 1.11–0.70 (CH₃), and others.

EXAMPLE 3

Synthesis of cyclo($_L$-aIle-$_L$-MeVal-$_L$-Leu-$_L$-βHOMeVal-$_D$-Hmp-$_L$-MeVal-$_L$-Cha-$_D$-MeAla-$_L$-Pro) (Compound 3)

a) Boc-$_L$-Cha-$_D$-MeAla-$_L$-Pro-OPac

The title compound was obtained as the same manner as Example 1 d) using Boc-$_L$-Cha-OH (137 mg, 0.507 mmol), HCl.H-$_D$-MeAla-$_L$-Pro-OPac (150 mg, 0.423 mmol), PyBroP (236 mg, 0.507 mmol) and DIEA (258 µl, 1.48 mmol). Yield 198 mg (82.1%).

b) HCl.H-$_L$-Cha-$_D$-MeAla-$_L$-Pro-OPaC

The title compound was obtained as the same manner as Example 1 e) using Boc-$_L$-Cha-$_D$-MeAla-$_L$-Pro-OPac (180 mg, 0.315 mmol) and 4.0N hydrogen chloride/dioxane (3.15 ml). Yield 148 mg (93.1%).

c) Boc-$_L$-aIle-$_L$-MeVal-$_L$-Leu-$_L$-βHOMeVal-$_D$-Hmp-$_L$-MeVal-$_L$-Cha-$_D$-MeAla-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (35.0 mg, 43.1 µmol), HCl.H-$_L$-Cha-$_D$-MeAla-$_L$-Pro-OPac (32.8 mg, 64.6 µmol), HOOBt (8.7 mg, 64.6 µl) and water soluble carbodiimide (11.4 µl, 64.6 µmol). Yield 48.6 mg (89.2%).

d) Boc-$_L$-aIle-$_L$-MeVal-$_L$-Leu-$_L$-βHOMeVal-$_D$-Hmp-$_L$-MeVal-$_L$-Cha-$_D$-MeAla-$_L$-Pro-OH

The title compound was obtained as the same manner as Example 1 t) using Boc-$_L$-aIle-$_L$-MeVal-$_L$-Leu-$_L$-

βHOMeVal-$_D$-Hmp-$_L$-MeVal-$_L$-Cha-$_D$-MeAla-$_L$-Pro-OPac (45.4 mg, 35.8 µmol), 90% acetic acid/water (1.6 ml) and zinc dust (466 mg, 7.16 mmol). Yield 46.0 mg.

e) HCl.H-$_L$-aIle-$_L$-MeVal-$_L$-Leu-$_L$-βHOMeVal-$_D$-Hmp-$_L$-MeVal-$_L$-Cha-$_D$-MeAla-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Cha-$_D$-MeAla-$_L$-Pro-OH (42.5 mg, 37.0 µmol), trifluoroacetic acid (570 µl, 7.40 mmol) and 4.0N hydrogen chloride/dioxane (18.5 µl, 74.0 µmol). Yield 31.7 mg (90.3%).

f) cyclo($_L$-aIle-$_L$-MeVal-$_L$-Leu-$_L$-βHOMeVal-$_D$-Hmp-$_L$-MeVal-$_L$-Cha-$_D$-MeAla-$_L$-Pro) (Compound 3)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Cha-$_D$-MeAla-$_L$-Pro-OH (25.0 mg, 21.1 µmol) and DIEA (7.3 µl, 42.2 µmol) in methylene chloride (10.6 ml), and solution of PyBroP (49.2 mg, 105.5 µmol) and DIEA (18.4 µl, 105.5 µmol) in methylene chloride (10.6 ml). Yield 6.8 mg (28.6%).

The physicochemical properties of the title compound are shown below.

$^1$H-NMR (CDCl$_3$, 270 MHz): δ8.62, 8.55, 7.92, 7.87, 7.75 (total 3H, NH), 5.82, 5.44–5.20, 5.02–4.86, 4.67, 4,56, 4.20, 4.03, 3.37 (total 10H), 3.29, 3.28, 3.27, 3.25, 3.24 (total 12H, NCH$_3$), 1.03–0.76 (CH$_3$), and others.

EXAMPLE 4

Synthesis of cyclo($_L$-aIle-$_L$-MeVal-$_L$-Leu-$_L$-βHOMeVal-$_D$-Hmp-$_L$-MeVal-$_L$-pFPhe-$_D$-MeAla-$_L$-Pro) (Compound 4)

a) Boc-$_L$-pFPhe-$_D$-MeAla-$_L$-Pro-OPac

The title compound was obtained as the same manner as Example 1 d) using Boc-$_L$-pFPhe-OH (100 mg, 0.353 mmol), HCl.H-$_D$-MeAla-$_L$-Pro-OPac (105 mg, 0.294 mmol), PyBroP (165 mg, 0.353 mmol) and DIEA (179 µl, 1.03 mmol). Yield 153 mg (89.2%).

b) HCl.H-$_L$-pFPhe-$_D$-MeAla-$_L$-Pro-OPac

The title compound was obtained as the same manner as Example 1 e) using Boc-$_L$-pFPhe-$_D$-MeAla-$_L$-Pro-OPac (140 mg, 0.240 mmol) and 4.0N hydrogen chloride/dioxane (2.4 ml). Yield 120 mg (96.8%).

c) Boc-$_L$-aIle-$_L$-MeVal-$_L$-Leu-$_L$-βHOMeVal-$_D$-Hmp-$_L$-MeVal-$_L$-pFPhe-$_D$-MeAla-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (35.0 mg, 43.1 µmol), HCl.H-$_L$-pFPhe-$_D$-MeAla-$_L$-Pro-OPac (33.6 mg, 64.6 µmol), HOOBt (8.7 mg, 64.6 µmol) and water soluble carbodiimide (11.4 µl, 64.6 µmol). Yield 48.8 mg (88.7%).

d) Boc-$_L$-aIle-$_L$-MeVal-$_L$-Leu-$_L$-βHOMeVal-$_D$-Hmp-$_L$-MeVal-$_L$-pFPhe-$_D$-MeAla-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-pFPhe-$_D$-MeAla-$_L$-Pro-OPac (45.3 mg, 35.4 µmol), 90% acetic acid/water (1.7 ml) and zinc dust (920 mg, 14.1 mmol). Yield 47.2 mg.

e) HCl.H-$_L$-aIle-$_L$-MeVal-$_L$-Leu-$_L$-B HOMeVal-$_D$-Hmp-$_L$-MeVal-$_L$-pFPhe-$_D$-MeAla-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-pFPhe-$_D$-MeAla-$_L$-Pro-OH (44.0 mg, 37.9 µmol), trifluoroacetic acid (584 µl, 7.58 mmol) and 4.0N hydrogen chloride/dioxane (18.9 µl, 75.8 µmol). Yield 34.9 mg (96.1%).

f) cyclo($_L$-aIle-$_L$-MeVal-$_L$-Leu-$_L$-βHOMeVal-$_D$-Hmp-$_L$-MeVal-$_L$-pFPhe-$_D$-MeAla-$_L$-Pro) (Compound 4)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-pFPhe-$_D$-MeAla-$_L$-Pro-OH (28.0 mg, 25.5 µmol) and DIEA (8.9 µl, 51.1 µmol) in methylene chloride (12.8 ml), and solution of PyBroP (59.4 mg, 128 µmol) and DIEA (22.2 µl, 128 µmol) in methylene chloride(12.8 ml). Yield 7.94 mg (29.8%).

The physicochemical properties of the title compound are shown below.

$^1$H-NMR (CDCl$_3$, 270 MHz): δ8.65, 7.98, 7.66 (total 3H, NH), 7.09–7.05 (total 4H, aromatic H), 5.84, 5.31, 5.19, 4.97, 4.88, 4.73–4.57, 4.17, 4.04, 3.44 (total 10H), 3.33, 3.32, 3.19, 2.94 (total 12H, NCH$_3$), 1.07–0.73 (CH$_3$), and others.

EXAMPLE 5

Synthesis of cyclo($_L$-aIle-$_L$-MeVal-$_L$-Leu-$_L$-βHOMeVal-$_D$-Hmp-$_L$-MeVal-$_L$-Leu-$_D$-MeAla-$_L$-Pro) (Compound 5)

a) Boc-$_L$-Leu-$_D$-MeAla-$_L$-Pro-OPac

The title compound was obtained as the same manner as Example 1 d) using Boc-$_L$-Leu-OH.H$_2$O (91.4 mg, 0.367 mmol), HCl.H-$_D$-MeAla-$_L$-Pro-OPac (100 mg, 0.282 mmol), PyBroP (171 mg, 0.367 mmol) and DIEA (197 µl, 1.13 mmol). Yield 124 mg (82.7%).

b) HCl.H-$_L$-Leu-$_D$-MeAla-$_L$-Pro-OPac

The title compound was obtained as the same manner as Example 1 e) using Boc-$_L$-Leu-$_D$-MeAla-$_L$-Pro-OPac (100 mg, 0.188 mmol) and 4.0N hydrogen chloride/dioxane (1.88 ml). Yield 80.4 mg (91.4%).

c) Boc-$_L$-aIle-$_L$-MeVal-$_L$-Leu-$_L$-βHOMeVal-$_D$-Hmp-$_L$-MeVal-$_L$-Leu-$_D$-MeAla-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (40.0 mg, 49.2 µmol), HCl.H-$_L$-Leu-$_D$-MeAla-$_L$-Pro-OPac (34.6 mg, 73.8 µmol), HOOBt (12.0 mg, 73.8 µl) and water soluble carbodiimide (13.1 µl, 73.8 µmol). Yield 33.5 mg (55.5%).

d) Boc-$_L$-aIle-$_L$-MeVal-$_L$-Leu-$_L$-βHOMeVal-$_D$-Hmp-$_L$-MeVal-$_L$-Leu-$_D$-MeAla-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Leu-$_D$-MeAla-$_L$-Pro-OPac (30.0 mg, 24.4 µmol), 90% acetic acid/water (1.5 ml) and zinc dust (350 mg, 4.88 mmol). Yield 25.1 mg.

e) HCl.H-$_L$-aIle-$_L$-MeVal-$_L$-Leu-$_L$-βHOMeVal-$_D$-Hmp-$_L$-MeVal-$_L$-Leu-$_D$-MeAla-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Leu-$_D$-MeAla-$_L$-Pro-OH (25.0 mg, 22.5 µmol), trifluoroacetic acid (347 µl, 4.50 mmol) and 4.0N hydrogen chloride/dioxane (8.5 µl, 33.8 µmol). Yield 21.2 mg (93.2%).

f) cyclo($_L$-aIle-$_L$-MeVal-$_L$-Leu-$_L$-βHOMeVal-$_D$-Hmp-$_L$-MeVal-$_L$-Leu-$_D$-MeAla-$_L$-Pro) (Compound 5)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Leu-$_D$-MeAla-$_L$-Pro-OH (19.0 mg, 18.2 µmol) and DIEA (6.3 µl, 36.4 µmol) in methylene chloride (9.1 ml), and solution of PyBroP (42.4 mg, 90.9 µmol) and DIEA (15.8 µl, 90.9 µmol) in methylene chloride (9.1 ml). Yield 7.1 mg (39.4%).

The physicochemical properties of the title compound are shown below.

$^1$H-NMR (CDCl$_3$, 270 MHz): δ8.60, 8.53, 7.88, 7.76, 7.69 (total 3H, NH), 5.77, 5.22, 4.98–4.80, 4.67, 4,56, 4.00 (total 11H), 3.38, 3.31, 3.29, 3.25, 3.24, 3.10 (total 12H, NCH$_3$), 1.16–0.76 (CH$_3$), and others.

EXAMPLE 6

Synthesis of cyclo($_L$-aIle-$_L$-MeVal-$_L$-Leu-$_L$-βHOMeVal-$_D$-Hmp-$_L$-MeVal-$_L$-Cha-$_L$-MePhe-$_L$-Pro) (Compound 6)

a) Boc-$_L$-Cha-$_L$-MePhe-$_L$-Pro-OPac

The title compound was obtained as the same manner as Example 1 d) using Boc-$_L$-Cha-OH (109 mg, 0.404 mmol), HCl.H-$_L$-MePhe-$_L$-Pro-OPac (150 mg, 0.336 mmol), PyBroP (188 mg, 0.404 mmol) and DIEA (205 μl, 1.18 mmol). Yield 201 mg (90.3%).

b) HCl.H-$_L$-Cha-$_L$-MePhe-$_L$-Pro-OPac

The title compound was obtained as the same manner as Example 1 e) using Boc-$_L$-Cha-$_L$-MePhe-$_L$-Pro-OPac (180 mg, 0.272 mmol) and 4.0N hydrogen chloride/dioxane (2.72 ml). Yield 103 mg (63.2%).

c) Boc-$_L$-aIle-$_L$-MeVal-$_L$-Leu-$_L$-βHOMeVal-$_D$-Hmp-$_L$-MeVal-$_L$-Cha-$_L$-MePhe-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (40.0 mg, 49.2 μmol), HCl.H-$_L$-Cha-$_L$-MePhe-$_L$-Pro-OPac (44.2 mg, 73.8 μmol), HOOBt (9.9 mg, 73.8 μl) and water soluble carbodiimide (13.0 μl, 73.8 μmol). Yield 45.9 mg (68.8%).

d) Boc-$_L$-aIle-$_L$-MeVal-$_L$-Leu-$_L$-βHOMeVal-$_D$-Hmp-$_L$-MeVal-$_L$-Cha-$_L$-MePhe-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Cha-$_L$-MePhe-$_L$-Pro-OPac (42.0 mg, 31.0 μmol), 90% acetic acid/water (2.0 ml) and zinc dust (402 mg, 6.19 mmol). Yield 46.1 mg.

e) HCl.H-$_L$-aIle-$_L$-MeVal-$_L$-Leu-$_L$-βHOMeVal-$_D$-Hmp-$_L$-MeVal-$_L$-Cha-$_L$-MePhe-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Cha-$_L$-MePhe-$_L$-Pro-OH (46.0 mg, 37.1 μmol), trifluoroacetic acid (570 μl, 7.42 mmol) and 4.0N hydrogen chloride/dioxane (14.0 μl, 55.7 μmol). Yield 43.5 mg (100%).

f) cyclo($_L$-aIle-$_L$-MeVal-$_L$-Leu-$_L$-βHOMeVal-$_D$-Hmp-$_L$-MeVal-$_L$-Cha-$_L$-MePhe-$_L$-Pro) (Compound 6)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Cha-$_L$-MePhe-$_D$-Pro-OH (25.0 mg, 21.3 μmol) and DIEA (7.4 μl, 42.5 μmol) in methylene chloride (10.5 ml), and solution of PyBroP (49.7 mg, 106.5 μmol) and DIEA (18.5 μl, 106.5 μmol) in methylene chloride (10.5 ml). Yield 5.7 mg (23.9%).

The physicochemical properties of the title compound are shown below.

$^1$H-NMR (CDCl$_3$, 270 MHz): δ8.68, 7.95, 7.88, 7.62 (total 3H, NH), 7.32–7.29, 7.17–7.15 (total 5H, aromatic H), 5.79, 5.72, 5.34, 5.25–4.81, 4.51, 4.23, 3.98, 3.38 (total 11H), 3.29, 3.27, 3.25, 3.20, 3.16, 3.13 (total 12H, NCH$_3$), 1.08–0.80 (CH$_3$), and others.

EXAMPLE 7

Synthesis of cyclo($_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro) (Compound 7)

a) Boc-$_L$-Ser(Bzl)-$_D$-MeAla-$_L$-Pro-OPac

The title compound was obtained as the same manner as Example 1 d) using Boc-$_L$-Ser(Bzl)-OH (106 mg, 0.360 mmol), HCl.H-$_D$-MeAla-$_L$-Pro-OPac (106 mg, 0.300 mmol), PyBroP (209 mg, 0.450 mmol) and DIEA (209 μl, 1.20 mmol). Yield 163 mg (91.4%).

b) HCl.H-$_L$-Ser(Bzl)-$_D$-MeAla-$_L$-Pro-OPac

The title compound was obtained as the same manner as Example 1 e) using Boc-$_L$-Ser(Bzl)-$_D$-MeAla-$_L$-Pro-OPac (150 mg, 0.252 mmol) and 4.0N hydrogen chloride/dioxane (2.52 ml). Yield 128 mg (95.4%).

c) Boc-$_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (50.0 mg, 61.5 μmol), HCl.H-$_L$-Ser(Bzl)-$_D$-MeAla-$_L$-Pro-OPac (49.0 mg, 92.2 μmol), HOOBt (12.5 mg, 92.2 μmol) and water soluble carbodiimide (16.3 μl, 92.2 μmol). Yield 61.2 mg (77.1%).

d) Boc-$_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro-OPac (50.0 mg, 38.7 μmol), 90% acetic acid/water (2.0 ml) and zinc dust (503 mg, 7.74 mmol). Yield 45.0 mg.

e) HCl.H-$_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro-OH (43.0 mg, 36.7 μmol), trifluoroacetic acid (560 μl, 7.34 mmol) and 4.0N hydrogen chloride/dioxane (13.7 μl, 55.1 μmol). Yield 34.0 mg (82.8%).

f) cyclo($_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro) (Compound 7)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Ser(Bzl)-$_D$-MeAla-$_L$-Pro-OH (30.0 mg, 27.1 μmol) and DIEA (9.4 μl, 54.1 μmol) in methylene chloride (13.5 ml), and solution of PyBroP (62.9 mg, 135.3 μmol) and DIEA (23.5 μl, 135 μmol) in methylene chloride (13.5 ml). Yield 12.9 mg (45.2%).

The physicochemical properties of the title compound are shown below.

$^1$H-NMR (CDCl$_3$, 270 MHz): δ8.47, 7.86, 7.76 (total 3H, NH), 7.32, 7.30 (total 5H, aromatic H), 5.78, 5.46–5.40, 5.21, 5.06, 4.93, 4.72–4.48, 4.18, 4.05–3.94, 3.65, 3.46, 3.38 (total 15H), 3.29, 3.27, 3.24, 3.23 (total 12H, NCH$_3$), 1.40–1.26, 0.99–0.77 (CH$_3$), and others.

EXAMPLE 8

Synthesis of cyclo($_L$-aIle-$_L$-MeVal-$_L$-Leu-$_L$-βHOMeVal-$_D$-Hmp-$_L$-MeVal-$_L$-Cha-$_D$-MeVal-$_L$-Pro) (Compound 8)

a) Boc-$_L$-Cha-$_D$-MeVal-$_L$-Pro-OPac

The title compound was obtained as the same manner as Example 1 d) using Boc-$_L$-Cha-OH (74.0 mg, 0.272 mmol), HCl.H-$_D$-MeVal-$_L$-MeVal-$_L$-Pro-OPac (80.0 mg, 0.209 mmol), PyBroP (127 mg, 0.272 mmol) and DIEA (146 μl, 0.836 mmol). Yield 107 mg (85.6%).

b) HCl.H-$_L$-Cha-$_D$-MeVal-$_L$-Pro-OPac

The title compound was obtained as the same manner as Example 1 u) using Boc-$_L$-Cha-$_D$-MeVal-$_L$-Pro-OPac (100 mg, 0.167 mmol) trifluoroacetate (515 μl, 6.68 mmol) and 4.0N hydrogen chloride/dioxane (125 μl, 0.501 mmol). Yield 75.1 mg (84.4%).

c) Boc-$_L$-aIle-$_L$-MeVal-$_L$-Leu-$_L$-βHOMeVal-$_D$-Hmp-$_L$-MeVal-$_L$-Cha-$_D$-MeVal-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (20.0 mg, 24.6 μmol), HCl.H-$_L$-Cha-$_D$-MeVal-$_L$-Pro-OPac (19.8 mg, 37.0 μmol), HOOBt (6.2 mg, 37.0 μmol) and water soluble carbodiimide (6.6 μl, 37.0 μmol). Yield 21.6 mg (67.9%).

d) Boc-$_L$-aIle-$_L$-MeVal-$_L$-Leu-$_L$-βHOMeVal-$_D$-Hmp-$_L$-MeVal-$_L$-Cha-$_D$-MeVal-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Cha-$_D$-MeVal-$_L$-Pro-OPac (36.2 mg, 27.9 μmol), 90% acetic acid/water (1.4 ml) and zinc dust (366 mg, 5.60 mmol). Yield 40.7 mg.

e) HCl.H-$_L$-aIle-$_L$-MeVal-$_L$-Leu-$_L$-βHOMeVal-$_D$-Hmp-$_L$-MeVal-$_L$-Cha-$_D$-MeVal-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Cha-$_D$-MeVal-$_L$-Pro-OH (37.7 mg, 32.1 μmol), trifluoroacetic acid (494 μl, 6.41 mmol) and 4.0N hydrogen chloride/dioxane (12.0 μl, 48.1 μmol). Yield 24.8 mg (86.4%).

f) cyclo($_L$-aIle-$_L$-MeVal-$_L$-Leu-$_L$-βHOMeVal-$_D$-Hmp-$_L$-MeVal-$_L$-Cha-$_D$-MeVal-$_L$-Pro) (Compound 8)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Cha-$_D$-MeVal-$_L$-Pro-OH (20.0 mg, 18.0 μmol) and DIEA (6.3 μl, 36.0 μmol) in methylene chloride (9.0 ml), and solution of PyBroP (42.0 mg, 89.9 μmol) and DIEA (15.7 μl, 89.9 μmol) in methylene chloride (9.0 ml). Yield 3.9 mg (20.5%).

The physicochemical properties of the title compound are shown below.

$^1$H-NMR (CDCl$_3$, 270 MHz): δ8.70, 8.02, 7.57 (total 3H, NH), 5.80, 5.44, 5.29–5.06, 4.99–4.80, 4.49, 4.31, 4.25, 4.09, 3.38 (total 11H), 3.29, 3.28, 3.27, 3.25, 3.08 (total 12H, NCH$_3$), 1.06–0.76 (CH$_3$), and others.

EXAMPLE 9

Synthesis of cyclo($_L$-aIle-$_L$-MeVal-$_L$-Leu-$_L$-βHOMeVal-$_D$-Hmp-$_L$-MeVal-$_L$-Cha-$_D$-MeSer-$_L$-Pro) (Compound 9)

a) Boc-$_L$-Cha-$_D$-MeSer(Bzl)-$_L$-Pro-OPac

The title compound was obtained as the same manner as Example 1 d) using Boc-$_L$-Cha-OH (99.6 mg, 0.365 mmol), HCl.H-$_D$-MeSer(Bzl)-$_L$-Pro-OPac (140 mg, 0.304 mmol), PyBroP (142 mg, 0.456 mmol) and DIEA (212 μl, 1.22 mmol). Yield 166 mg (80.5%).

b) HCl.H-$_L$-Cha-$_D$-MeSer(Bzl)-$_L$-Pro-OPac

The title compound was obtained as the same manner as Example 1 e) using Boc-$_L$-Cha-$_D$-MeSer(Bzl)-$_L$-Pro-OPac (160 mg, 0.235 mmol) and 4.0N hydrogen chloride/dioxane (2.94 ml). Yield 132 mg (91.0%).

c) Boc-$_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (60.0 mg, 73.8 μmol), HCl.H-$_L$-Cha-$_D$-MeSer(Bzl)-$_L$-Pro-OPac (67.7 mg, 0.110 mmol), HOOBt (18.1 mg, 0.110 mol) and water soluble carbodiimide (19.5 μl, 0.110 mmol). Yield 81.9 mg (80.7%).

d) Boc-$_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro-OPac (143 mg, 0.104 mmol), 90% acetic acid/water (5.0 ml) and zinc dust (1.35 g, 20.8 mmol). Yield 123 mg.

e) HCl.H-$_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro-OH (70.0 mg, 55.7 μmol), trifluoroacetic acid (855 μl, 11.1 mmol) and 4.0N hydrogen chloride/dioxane (27.8 μl, 0.111 mmol). Yield 51.9 mg (78.0%).

f) cyclo($_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro-OH (48.0 mg, 40.2 μmol) and DIEA (14.0 μl, 80.5 μmol) in methylene chloride (20.1 ml), and solution of PyBroP (93.7 mg, 0.201 mmol) and DIEA (35.0 μl, 0.201 mmol) in methylene chloride (20.1 ml). Yield 15.7 mg (34.3%).

The physicochemical properties of the title compound are shown below.

$^1$H-NMR (CDCl$_3$, 270 MHz): δ8.55, 7.90, 7.68 (total 3H, NH), 7.32–7.26 (total 5H, aromatic H), 5.81, 5.43, 5.42, 5.27–5.19, 5.02–4.81, 4.68, 4.55, 4.21, 3.99, 3.88, 3.37 (total 13H), 3.30, 3.29, 3.26, 3.25, 3.23, 3.08 (total 12H, NCH$_3$), 1.03–0.76 (CH$_3$), and others.

g) cyclo($_L$-aIle-$_L$-MeVal-$_L$-Leu-$_L$-βHOMeVal-$_D$-Hmp-$_L$-MeVal-$_L$-Cha-$_D$-MeSer-$_L$-Pro) (Compound 9)

To cyclo($_L$-aIle-$_L$-MeVal-$_L$-Leu-$_L$-βHOMeVal-$_D$-Hmp-$_L$-MeVal-$_L$-Cha-$_D$-MeSer(Bzl)-$_L$-Pro) (11.6 mg, 10.2 μmol) in methanol (1.5 ml) was added palladium black (15 mg), and hydrogen gas was blown in for 2 hours at room temperature, and an additional 1 hour at 30° C. After filtering out the catalyst and concentrating under reduced pressure, the residue was purified by preparative silica gel thin layer chromatography (developed and extracted with chloroform-methanol 19:1) to provide the title compound. Yield 8.6 mg (80.5%).

The physicochemical properties of the title compound are shown below.

$^1$H-NMR (CDCl$_3$, 270 MHz): δ8.63, 8.56, 7.90, 7.76 (total 3H, NH), 5.81, 5.42, 5.28, 5.21, 4.98, 4.90, 4.70–4.56, 4.21, 4.10–4.03, 3.37 (total 13H), 3.39, 3.29, 3.26, 3.25, 3.23 (total 12H, NCH$_3$), 1.02–0.76 (CH$_3$), and others.

EXAMPLE 10

Synthesis of cyclo($_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro) (Compound 10)

a) Boc-$_L$-Tyr(Bzl)-$_D$-MeAla-$_L$-Pro-OPac

The title compound was obtained as the same manner as Example 1 d) using Boc-$_L$-Tyr(Bzl)-OH (680 mg, 1.83 mmol), HCl.H-$_D$-MeAla-$_L$-Pro-OPac (500 mg, 1.48 mmol), PyBroP (853 mg, 1.83 mmol) and DIEA (981 μl, 5.63 mmol). Yield 827 mg (87.4%).

b) HCl.H-$_L$-Tyr(Bzl)-$_D$-MeAla-$_L$-Pro-OPac

The title compound was obtained as the same manner as Example 1 e) using Boc-$_L$-Tyr(Bzl)-$_D$-MeAla-$_L$-Pro-OPac (428 mg, 0.636 mmol) and 4.0N hydrogen chloride/dioxane (6.36 ml). Yield 355 mg (91.6%).

c) Boc-$_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (100 mg, 0.123 mmol), HCl.H-$_L$-Tyr(Bzl)-$_D$-MeAla-$_L$-Pro-OPac (112 mg, 0.184 mmol), HOOBt (30.1 mg, 0.184 mmol) and water soluble carbodiimide (32.7 μl, 0.184 mmol). Yield 125 mg (74.3%).

d) Boc-$_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro-OPac (85.0 mg, 62.1 μmol), 90% acetic acid/water (3.0 ml) and dust powder (808 mg, 12.4 mmol). Yield 77.6 mg.

e) HCl.H-$_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro-OH

The title compound was obtained as the same manner as Example 1 u) using Boc-$_L$-aIle-$_L$-MeVal-$_L$-Leu-$_L$-

βHOMeVal-$_D$-Hmp-$_L$-MeVal-$_L$-Tyr(Bzl)-$_D$-MeAla-$_L$-Pro-OH (77.6 mg, 62.1 µmol), trifluoroacetic acid (220 µl, 2.84 mmol) and 4.0N hydrogen chloride/dioxane (23.3 µl, 93.2 µmol). Yield 70.8 mg (96.1%).

f) cyclo($_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro) (Compound 10)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro-OH (70.8 mg, 59.7 µmol) and DIEA (20.8 µl, 0.119 mmol) in methylene chloride (30.0 ml), and solution of PyBroP (139 mg, 0.298 mmol) and DIEA (52.0 µl, 0.298 mmol) in methylene chloride (30.0 ml). Yield 28.0 mg (41.5%).

The physicochemical properties of the title compound are shown below.

$^1$H-NMR (CDCl$_3$, 270 MHz): δ8.65, 8.02, 7.72 (total 3H, NH), 7.53–7.29, 7.03 (total 9H, aromatic H), 5.83, 5.32, 5.20–4.91, 4.69–4.57, 4.25, 4.04, 3.43 (total 13H), 3.32, 3.20, 2.97, 2.94 (total 12H, NCH$_3$), 1.08–0.74 (CH$_3$), and others.

EXAMPLE 11

Synthesis of cyclo($_L$-aIle-$_L$-MeVal-$_L$-Leu-$_L$-βHOMeVal-$_D$-Hmp-$_L$-MeVal-$_L$-Tyr(Me)-$_D$-MeAla-$_L$-Pro) (Compound 11)

a) cyclo($_L$-aIle-$_L$-MeVal-$_L$-Leu-$_L$-βHOMeVal-$_D$-Hmp-$_L$-MeVal-$_L$-Tyr-$_D$-MeAla-$_L$-Pro)

To cyclo($_L$-aIle-$_L$-MeVal-$_L$-Leu-$_L$-βHOMeVal-$_D$-Hmp-$_L$-MeVal-$_L$-Tyr(Bzl)-$_D$-MeAla-$_L$-Pro) (28.0 mg, 24.7 µmol) in methanol(30 ml) was added palladium black (15 mg), and hydrogen gas was blown in for 4 hours at room temperature. After filtering out the catalyst and concentrating under reduced pressure, the residue was purified by preparative silica gel thin layer chromatography (developed and extracted by chloroform-methanol 19:1) to provide the title compound. Yield 18.2 mg (90.6%).

The physicochemical properties of the title compound are shown below.

$^1$H-NMR (CDCl$_3$, 270 MHz): δ8.52, 7.89, 7.56 (total 3H, NH), 6.86 (total 4H, aromatic H), 5.75, 5.40, 5.21, 5.02, 4.79, 4.75, 4.66, 4.54, 4.31, 4.06, 3.53 (total 11H), 3.37, 3.32, 3.23, 2.73 (total 12H, NCH$_3$), 1.07–0.69 (CH$_3$), and others.

b) cyclo($_L$-aIle-$_L$-MeVal-$_L$-Leu-$_L$-βHOMeVal-$_D$-Hmp-$_L$-MeVal-$_L$-Tyr(Me)-$_D$-MeAla-$_L$-Pro) (Compound 11)

To cyclo($_L$-aIle-$_L$-MeVal-$_L$-Leu-$_L$-βHOMeVal-$_D$-Hmp-$_L$-MeVal-$_L$-Tyr-$_D$-MeAla-$_L$-Pro) (3.0 mg, 2.88 µmol) in methanol-acetonitrile (1:9) (100 µl) was added DIEA (0.7 µl, 4.04 µmol) and trimethylsilyldiazomethane (4.9 µl, 43.2 µmol). The obtained mixture was stirred for 8 hours at room temperature and concentrated under reduced pressure. The residue was purified by preparative silica gel thin layer chromatography (developed and extracted by chloroform-methanol 19:1) to provide the title compound. Yield 2.1 mg (69.1%).

The physicochemical properties of the title compound are shown below.

$^1$H-NMR (CDCl$_3$, 270 MHz): δ8.65, 8.04, 7.74 (total 3H, NH), 7.04, 6.90 (total 4H, aromatic H), 5.83, 5.31, 5.18, 4.94, 4.67, 4.60, 4.23, 4.04, 3.47, 3.41 (total 13H), 3.82 (3H, OCH$_3$), 3.32, 3.31, 3.20, 2.99 (total 12H, NCH$_3$), 1.07–0.75 (CH$_3$), and others.

EXAMPLE 12

Synthesis of cyclo($_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro) (Compound 12)

a) Boc-$_L$-Tyr(c-C$_6$H$_{11}$—CH$_2$—)—OH

Under ice-cooling, 60% sodium hydride (229 mg, 5.73 mmol) was added to Boc-$_L$-Tyr-OH (500 mg, 2.29 mmol) in DMF(4.6 ml). The mixture was stirred for 1 hour under ice-cooling, then added cyclohexylmethyl bromide (317 µl, 3.44 mmol). The resulting mixture was stirred for 5 hours under ice-cooling. After concentrating under reduced pressure, the residue was adjusted the pH to 4 with 10% citric acid in water and extracted with ethyl acetate. The extract was washed with saturated sodium chloride-H$_2$O, dried over magnesium sulfate and concentrated under reduced pressure to provide the title compound. Yield 269 mg (37.3%).

b) Boc-$_L$-Tyr(c-C$_6$H$_{11}$—CH$_2$—)-$_D$-MeAla-$_L$-Pro-OPac

The title compound was obtained as the same manner as Example 1 d) using Boc-$_L$-Tyr(c-C$_6$H$_{11}$—CH$_2$—)—OH (138 mg, 0.366 mmol), HCl.H-$_D$-MeAla-$_L$-Pro-OPac (100 mg, 0.282 mmol), PyBroP (171 mg, 0.366 mmol) and DIEA (197 µl, 1.13 mmol). Yield 136 mg (71.2%).

c) HCl.H-$_L$-Tyr(c-C$_6$H$_{11}$—CH$_2$—)-$_D$-MeAla-$_L$-Pro-OPac

The title compound was obtained as the same manner as Example 1 e) using Boc-$_L$-Tyr(c-C$_6$H$_{11}$—CH$_2$—)-$_D$-MeAla-$_L$-Pro-OPac (136 mg, 0.198 mmol) and 4.0N hydrogen chloride/dioxane (1.98 ml). Yield 111 mg (90.0%).

d) Boc-$_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro-OPac

The title compound was obtained as the same manner as Example 1 s) using Boc-$_L$-aIle-$_L$-MeVal-$_L$-Leu-$_L$-βHOMeVal-$_D$-Hmp-$_L$-MeVal-OH (30.0 mg, 36.9 µmol), HCl.H H-$_L$-Tyr(c-C$_6$H$_{11}$—CH$_2$—)-$_D$-MeAla-$_L$-Pro-OPac (33.9 mg, 55.3 µmol), HOOBt (9.0 mg, 55.3 µmol) and water soluble carbodiimide (9.8 µl, 55.3 µmol). Yield 46.2 mg (91.2%).

e) Boc-$_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro-OH

The title compound was obtained as the same manner as Example 1 t) using Boc-$_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro-OPac (43.3 mg, 31.5 µmol), 90% acetic acid/water (1.0 ml) and zinc dust (410 mg, 6.31 mmol). Yield 37.4 mg.

f) HCl.H-$_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro-OH

The title compound was obtained as the same manner as Example 1 u) using Boc-$_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro-OH (37.4 mg, 29.8 µmol), trifluoroacetic acid (92.0 µl, 1.19 mmol) and 4.0N hydrogen chloride/dioxane (11.2 µl, 44.7 µmol). Yield 28.7 mg (80.8%).

g) cyclo($_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro) (Compound 12)

The title compound was obtained as the same manner as Example 1 v) using solution of HCl.H-$_L$-aIle-$_L$-MeVal-$_L$-Leu-$_L$-βHOMeVal-$_D$-Hmp-$_L$-MeVal-$_L$-Tyr(c-C$_6$H$_{11}$—CH$_2$—)-$_D$-MeAla-$_L$-Pro-OH (25.0 mg, 20.9 µmol) and DIEA (7.3 µl, 41.9 µmol) in methylene chloride (10.5 ml), and solution of PyBroP (46.8 mg, 0.105 mmol) and DIEA (18.3 µl, 0.105 mmol) in methylene chloride (10.5 ml). Yield 12.5 mg (52.3%).

The physicochemical properties of the title compound are shown below.

$^1$H-NMR (CDCl$_3$, 270 MHz): δ8.70, 8.07, 7.78 (total 3H, NH), 7.05, 6.85 (total 4H, aromatic H), 5.85, 5.30, 5.18, 4.96, 4.68, 4.64, 4.58, 4.27, 4.04, 3.77, 3.42 (total 13H), 3.32, 3.18, 3.02 (total 12H, NCH$_3$), 1.07–0.75 (CH$_3$), and others.

The elementary analysis, FABMS and amino acid analysis of the resulting compound 1 to 12 and their biological properties were as follows.

(1) The results of the elementary analysis, FABMS and amino acid analysis

The results of the elementary analysis, FABMS and amino acid analysis are shown in Table 2. The amino acid analysis was conducted using Nippondenshi JCL-300 and detected by ninhydrine reaction.

TABLE 2

| Compound Number | Molecular Formula | Elementary Analysis (%) Found/Anal. Calcd | | | FABMS | Amino Acid Analysis |
|---|---|---|---|---|---|---|
| | | C | H | N | | |
| 1 | C$_{54}$H$_{33}$N$_8$O$_{11}$ | 62.59 | 8.81 | 10.73 | 1025 (M+H), | Pro, alle, |
| | | 63.26 | 8.65 | 10.93 | 1047 (M+Na) | Leu, Phe |
| 2 | C$_{56}$H$_{92}$N$_8$O$_{11}$ | 61.93 | 9.08 | 10.18 | 1053 (M+H), | Pro, alle, |
| | | 63.85 | 8.80 | 10.64 | 1075 (M+Na) | Leu, Phe |
| 3 | C$_{54}$H$_{94}$N$_8$O$_{11}$ | 61.91 | 9.28 | 10.39 | 1031 (M+H), | Pro, alle, |
| | | 62.89 | 9.19 | 10.86 | 10.53 (M+Na) | Leu, Cha |
| 4 | C$_{54}$H$_{87}$N$_8$O$_{11}$F | 64.38 | 8.19 | 10.01 | 1043 (M+H), | Pro, alle, |
| | | 62.17 | 8.40 | 10.74 | 1065 (M+Na) | Leu, pFPhe |
| 5 | C$_{51}$H$_{90}$N$_8$O$_{11}$ | 61.85 | 9.34 | 11.02 | 991 (M+H), | Pro, alle, |
| | | 61.79 | 9.15 | 11.30 | 1013 (M+Na) | Leu |
| 6 | C$_{60}$H$_{98}$N$_8$O$_{11}$ | 65.17 | 8.68 | 10.43 | 1107 (M+H), | Pro, alle, |
| | | 65.07 | 8.92 | 10.12 | 1129 (M+Na) | Leu, Cha |
| 7 | C$_{55}$H$_{90}$N$_8$O$_{12}$ | 62.39 | 8.83 | 10.46 | 1055 (M+H), | Pro, alle, |
| | | 62.60 | 8.60 | 10.62 | 1077 (M+Na) | Leu, Ser |
| 8 | C$_{56}$H$_{98}$N$_8$O$_{11}$ | 63.82 | 9.04 | 10.86 | 1059 (M+H), | Pro, alle, |
| | | 63.48 | 9.32 | 10.58 | 1081 (M+Na) | Leu, Cha |
| 9 | C$_{54}$H$_{84}$N$_8$O$_{12}$ | 62.31 | 8.86 | 10.91 | 1047 (M+H), | Pro, alle, |
| | | 61.93 | 9.05 | 10.70 | 1069 (M+Na) | Leu, Cha |
| 10 | C$_{61}$H$_{94}$N$_8$O$_{12}$ | 64.46 | 8.65 | 9.44 | 1131 (M+H), | Pro, alle, |
| | | 64.75 | 8.37 | 9.90 | 1153 (M+Na) | Leu |
| 11 | C$_{55}$H$_{90}$N$_8$O$_{12}$ | 62.97 | 8.51 | 10.75 | 1055 (M+H), | Pro, alle, |
| | | 62.60 | 8.60 | 10.62 | 1077 (M+Na) | Leu |
| 12 | C$_{61}$H$_{100}$N$_8$O$_{12}$ | 63.92 | 8.47 | 10.17 | 1137 (M+H), | Pro, alle, |
| | | 64.41 | 8.86 | 9.85 | 1159 (M+Na) | Leu |

(2) Biological property

Minimum growth inhibiting concentration (MIC, µg/ml) against fungi of Compound 1 to 12 are shown in Table 3 and Table 4. MIC was measured by agarose plate dilution method (cultivated at 30° C. for 2 days) using saburo-dextrose agarose culture (glucose 2 W/V %, polipeptone 1 W/V %, agarose 1.5 W/V %). Control was Aureobasidin A (AbA).

TABLE 3

| | MIC (µg/ml) | | | | | |
|---|---|---|---|---|---|---|
| | | Compound Number | | | | |
| Eumycetes Tested | AbA | 1 | 2 | 3 | 4 | 5 |
| Candida albicans TIMM0136 | 0.025 | 0.05 | 0.025 | 0.0125 | 0.10 | 0.10 |
| Candida albicans TIMM0171 | 0.025 | 0.05 | 0.025 | 0.025 | 0.05 | 0.05 |
| Candida kefyr TIMM0301 | 0.39 | 0.20 | 0.20 | 0.20 | 0.20 | 0.20 |
| Candida glabrata TIMM1062 | 0.20 | 0.20 | 0.20 | 0.10 | 0.20 | 0.20 |

TABLE 3-continued

| | MIC (µg/ml) | | | | | |
|---|---|---|---|---|---|---|
| | | Compound Number | | | | |
| Eumycetes Tested | AbA | 1 | 2 | 3 | 4 | 5 |
| Cryptococcus neoformans TIMM0354 | 0.78 | 3.12 | 1.56 | 0.10 | 3.12 | 0.39 |
| Aspergillus fumigatus TIMM2766 | >25 | 12.5 | 6.25 | 3.12 | 12.5 | 25 |

TABLE 4

| | MIC (µg/ml) | | | | | | | |
|---|---|---|---|---|---|---|---|---|
| | | Compound Number | | | | | | |
| Eumycetes Tested | AbA | 6 | 7 | 8 | 9 | 10 | 11 | 12 |
| Candida albicans TIMM0136 | 0.025 | 0.39 | 0.10 | 0.10 | 0.20 | 0.05 | 0.10 | 0.10 |
| Candida albicans TIMM0171 | 0.025 | 0.20 | 0.05 | 0.05 | 0.20 | 0.05 | 0.10 | 0.39 |

TABLE 4-continued

| Eumycetes Tested | MIC (μg/ml) | | | | | | | |
|---|---|---|---|---|---|---|---|---|
| | AbA | 6 | 7 | 8 | 9 | 10 | 11 | 12 |
| Candida kefyr TIMM0301 | 0.39 | 1.56 | 0.78 | 0.78 | 0.78 | 0.78 | 0.39 | 1.56 |
| Candida glabrata TIMM1062 | 0.20 | 1.56 | 0.78 | 0.78 | 0.78 | 1.56 | 0.39 | 0.39 |
| Cryptococcus neoformans TIMM0354 | 0.78 | 0.20 | 0.39 | 0.39 | 0.20 | 0.78 | 0.78 | 0.20 |
| Aspergillus fumigatus TIMM2766 | >25 | >25 | >25 | >25 | >25 | 1.56 | 12.5 | 1.56 |

Compound 1 to 5, 10 to 12 had activity for Aspergillus at the concentration of 1.56 to 25 μg/ml. For Cryptococcus, compound 3, 5 to 9 and 12 had activity at the concentration of 0.10 to 0.39 μg/ml. In particular, compound 3 and 12 had activity for Aspergillus at 3.12 μg/ml and 1.56 μg/ml respectively, and also showed strong activity for Cryptococcus, having stronger activity than Aureobasidin A.

Further, compound 1 to 12 was administered intraperitoneally to ICR mouse at a dose of 100 mg/kg, but no toxicity was detected.

From these biological properties, the compounds of this invention were found to be effective for treatment of many kinds of mycosis such as one caused by Cryptococcus, Aspergillus or the like.

INDUSTRIAL APPLICABILITY

The compound according to this invention has an excellent activity against not only Candida but also at least one of Cryptococcus and Aspergillus, thus has much effective applicability for antifungal agent having broader spectrum.

We claim:

1. An Aureobasidin compound of general formula (1):

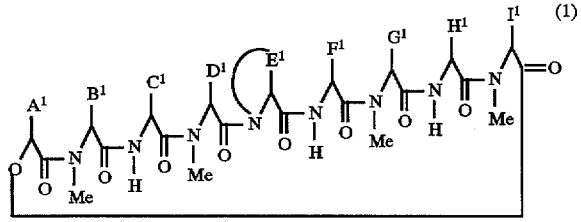

wherein $A^1$, $B^1$, $F^1$, $G^1$ and $H^1$ are the same or different from each other and each represents a straight-chain or branched lower alkyl having 1 to 6 carbon atoms; $C^1$ represents a straight-chain or branched lower alkyl having 1 to 6 carbon atoms, a cycloalkyl group having 3 to 7 carbon atoms, benzyloxymethyl, benzyl, a substituted benzyl, phenyl or a substituted phenyl (said substituted benzyl or substituted phenyl means benzyl or phenyl substituted by at least one substituent selected from a straight-chain or branched lower alkoxy having 1 to 6 carbon atoms, cycloalkoxy having 3 to 7 carbon atoms, benzyloxy and halogen); $D^1$ represents a straight-chain or branched lower alkyl having 1 to 6 carbon atoms, hydroxymethyl or benzyl (where $C^1$ is benzyl, ortho-fluorobenzyl, or meta-fluorobenzyl, $D^1$ is a group other than benzyl and hydroxymethyl); $E^1$ represents a straight-chain alkylene having 1 to 5 carbon atoms; $I^1$ represents a hydroxy-substituted lower alkyl having 1 to 6 carbon atoms.

2. The Aureobasidin compound according to claim 1, wherein;

said $A^1$ is $(CH_3)_2CH-$ or $CH_3CH_2CH(CH_3)-$, said $B^1$ is $(CH_3)_2CH-$, said $C^1$ is a straight-chain or branched lower alkyl having 1 to 6 carbon atoms, a cycloalkyl having 3 to 7 carbon atoms, benzyloxymethyl, benzyl, a substituted benzyl, phenyl or a substituted phenyl (said substituted benzyl or substituted phenyl means benzyl or phenyl substituted by at least one substituent selected from a straight-chain or branched lower alkoxy having 1 to 6 carbon atoms, cycloalkoxy having 3 to 7 carbon atoms, benzyloxy and halogen), said $D^1$ is a straight-chain or branched lower alkyl group having 1 to 6 carbon atoms, hydroxymethyl or benzyl (where $C^1$ is benzyl, ortho-fluorobenzyl, or meta-fluorobenzyl, $D^1$ is not benzyl and hydroxymethyl), said $E^1$ is $-(CH_2)_3-$, said $F^1$ is $(CH_3)_2CH-$, $(CH_3)_2CHCH_2-$ or $CH_3CH_2CH(CH_3)-$, said $G^1$ is $(CH_3)_2CH-$, said $H^1$ is $(CH_3)_2CH-$, $(CH_3)_2CHCH_2-$ or $CH_3CH_2CH(CH_3)-$, and, said $I^1$ is $(CH_3)_2C(OH)-$.

3. The Aureobasidin compound according to claim 2, wherein;

said $A^1$ is $(CH_3)_2CH-$ or $CH_3CH_2CH(CH_3)-$, said $B^1$ is $(CH_3)_2CH-$, said $C^1$ is $CH_3-$, $(CH_3)_2CH-$, $(CH_3)_2CHCH_2-$, $CH_3CH_2CH(CH_3)-$, cyclohexylmethyl, benzyloxymethyl, benzyl or a substituted benzyl (said substituted benzyl means benzyl or phenyl substituted by at least one substituent selected from a straight-chain or branched lower alkoxy having 1 to 6 carbon atoms, cycloalkoxy having 3 to 7 carbon atoms, benzyloxy and halogen), said $D^1$ is $CH_3-$, $(CH_3)_2CH-$, $(CH_3)_2CHCH_2-$, $CH_3CH_2CH(CH_3)-$, hydroxymethyl or benzyl (where $C^1$ is benzyl, ortho-fluorobenzyl, or meta-fluorobenzyl, $D^1$ is not benzyl and hydroxymethyl), said $E^1$ is $-(CH_2)_3-$, said $F^1$ is $(CH_3)_2CH-$, $(CH_3)_2CHCH_2-$ or $CH_3CH_2CH(CH_3)-$, said $G^1$ is $(CH_3)_2CH-$, said $H^1$ is $(CH_3)_2CH-$, $(CH_3)_2CHCH_2-$ or $CH_3CH_2CH(CH_3)-$, and, said $I^1$ is $(CH_3)_2C(OH)-$.

* * * * *